United States Patent [19]

Weerasooriya et al.

[11] Patent Number: 5,386,045
[45] Date of Patent: * Jan. 31, 1995

[54] PROCESS FOR ALKOXYLATION OF ESTERS AND PRODUCTS PRODUCED THEREFROM

[75] Inventors: Upali Weerasooriya; Donald T. Robertson, both of Austin; John Lin, Cedar Park; Bruce E. Leach, Austin; Cynthia L. Aeschbacher, Austin; Tonyette S. Sandoval, Austin, all of Tex.

[73] Assignee: Vista Chemical Company, Houston, Tex.

[*] Notice: The portion of the term of this patent subsequent to Jun. 15, 2010 has been disclaimed.

[21] Appl. No.: 924,952

[22] Filed: Aug. 5, 1992

Related U.S. Application Data

[63] Continuation-in-part of Ser. No. 748,449, Aug. 22, 1991, Pat. No. 5,220,046.

[51] Int. Cl.[6] ............................. C07C 69/96

[52] U.S. Cl. .................. 554/149; 554/227; 560/180; 560/186; 560/200; 568/618; 568/619; 502/167

[58] Field of Search ............... 502/167; 568/618, 619; 554/149, 227; 560/180, 186, 200

[56] References Cited

U.S. PATENT DOCUMENTS

| 4,775,653 | 10/1988 | Leach et al. | 502/170 |
| 4,820,673 | 4/1989 | Knopf et al. | 502/167 |
| 5,191,104 | 3/1993 | King | 558/260 |
| 5,220,046 | 6/1993 | Leach et al. | 554/149 |

FOREIGN PATENT DOCUMENTS

3914131 10/1990 Germany .

Primary Examiner—José G. Dees
Assistant Examiner—D. D. Carr
Attorney, Agent, or Firm—Browning, Bushman, Anderson & Brookhart

[57] ABSTRACT

A process for producing alkoxylated mono-, di-, and tri-esters in which a starting material ester and an alkylene oxide are reacted in the presence of selected calcium based catalysts.

25 Claims, 3 Drawing Sheets

PROCESS FOR ALKOXYLATION OF ESTERS AND PRODUCTS PRODUCED THEREFROM

BACKGROUND OF THE INVENTION

This is a continuation in part of co-pending application, Ser. No. 07/748,449, filed Aug. 22, 1991, now U.S. Pat. No. 5,220,046.

1. Field of the Invention

The present invention relates to a process for producing alkoxylated esters and, more particularly, to a process for producing such esters having a narrow homolog distribution of the alkoxylated ester.

2. Description of the Prior Art

Alkoxylated esters, e.g. alkoxylated esters of fatty acids, are well known and find use in surfactant and other applications. Such esters can be prepared by various techniques well known in the art. For example, German reference DE 3914131 describes the alkoxylation of fatty acid esters using calcined hydrotalcites as catalysts. It is also well known to prepare such alkoxylated fatty acid esters using sodium hydroxide/alcohol and sodium methoxide catalysts. The use of catalysts such as sodium hydroxide and sodium methoxide results in the production of alkoxylated esters having a broad homolog distribution of the alkoxylated product. Additionally, the reaction times using these catalysts is slow and conversions are low. Although the use of hydrotalcite, as discussed in the above referenced German patent publication, is claimed to produce the alkoxylated fatty acid ester in high yield with a narrow homolog distribution, the distribution of the end product cannot be considered truly "peaked," i.e., with the desired narrow distribution of homologs.

U.S. Pat. No. 4,820,673 discloses a calcium-based catalyst for use in the alkoxylation of organic compounds having at least one active hydrogen to provide end products having a narrow distribution of the alkoxylation species.

U.S. Pat. No. 4,835,321 discloses another type of calcium-based catalyst for the alkoxylation of alcohols to provide alkoxylated alcohols having a narrow distribution of the alkoxylation species.

SUMMARY OF THE INVENTION

It is therefore an object of the present invention to provide an improved process for producing alkoxylated esters of fatty acids.

Another object of the present invention is to provide a process for producing alkoxylated methyl esters of fatty acids wherein the product has a narrow distribution of the alkoxylation species.

Still a further object of the present invention is to provide a process for the production of alkoxylated esters, particularly methyl esters, of fatty acids that requires a relatively small amount of catalyst, has a relatively short reaction time and exhibits a high level of conversion of starting material.

A further object of the present invention is to provide a novel composition of alkoxylated methyl esters having a narrow distribution of the alkoxylation species.

The above and other objects of the present invention will become apparent from the drawings, the description given herein and the appended claims.

According to the process of the present invention, alkoxylated esters selected from the group consisting of alkoxylated monoesters having the formula:

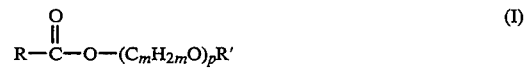

alkoxylated ethylene glycol diesters having the formula:

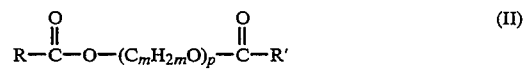

and alkoxylated triesters having the formula:

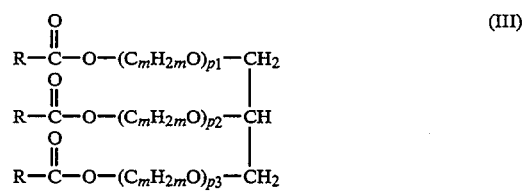

wherein m is from 2 to 4, $p_1$, $p_2$ and $p_3$ are each from about 1 to about 50, and R and R' are each organic radicals containing from about 1 to about 30 carbon atoms are prepared. In the process, an alkylene oxide containing from 2 to 4 carbon atoms is reacted with a compound selected from the group consisting of monoesters having the formula:

ethylene glycol diesters having the formula:

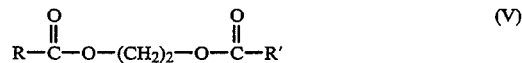

and triesters having the formula:

respectively,

The reaction is conducted at a temperature of from about 80° to about 200° C. and at a pressure which can range from sub-ambient up to about 100 psi or higher. A catalytically effective amount of a calcium catalyst is employed in the reaction. The catalyst is selected from the group consisting of (1) Calcium Catalyst A formed by reacting a reactant mixture comprising an alkoxylated alcohol mixture containing compounds having the general formula:

wherein $R_1$ is an organic radical containing from about 1 to about 30 carbon atoms, a calcium-containing compound which is at least partially dispersible in said alkoxylated alcohol mixture, an inorganic acid, and a metal alkoxide selected from compounds having the formulas:

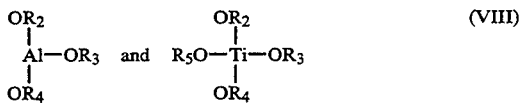
(VIII)

wherein $R_2$, $R_3$, $R_4$ and $R_5$ is each a hydrocarbon radical containing from about 1 to about 30 carbon atoms, said calcium-containing compound and said alkoxylated alcohol mixture being mixed prior to addition of said metal alkoxide, said reactant mixture being heated to a temperature and for a time sufficient to effect at least a partial exchange reaction between the alkoxide groups of said metal alkoxide and said hydroxyl groups of said alkoxylated alcohol (2) Calcium Catalyst B formed by solubilizing, at least partially, a calcium-containing compound with an activator having the formula:

$$Z_a\text{—}X\text{—}Q\text{—}Y\text{—}Z'_b \quad (IX)$$

wherein X and Y are the same or different electronegative, hetero-atoms selected from the group consisting of oxygen, nitrogen, sulfur and phosphorus; a and b are the same or different integers satisfying the valency requirements of X and Y; Q is an organic radical which is electropositive or essentially neutral relative as to X and/or Y; Z and Z' are the same or different and are either hydrogen or an organic radical which does not prevent said solubilizing, and mixtures of Calcium Catalyst A and Calcium Catalyst B.

In another aspect of the invention, there is produced a novel composition of matter comprising an alkoxylated methyl ester having the formula:

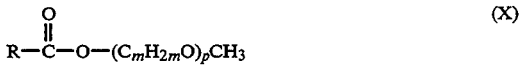
(X)

which has a highly peaked distribution of the alkoxylated species.

DESCRIPTION OF THE PREFERRED EMBODIMENTS

Figure 1:
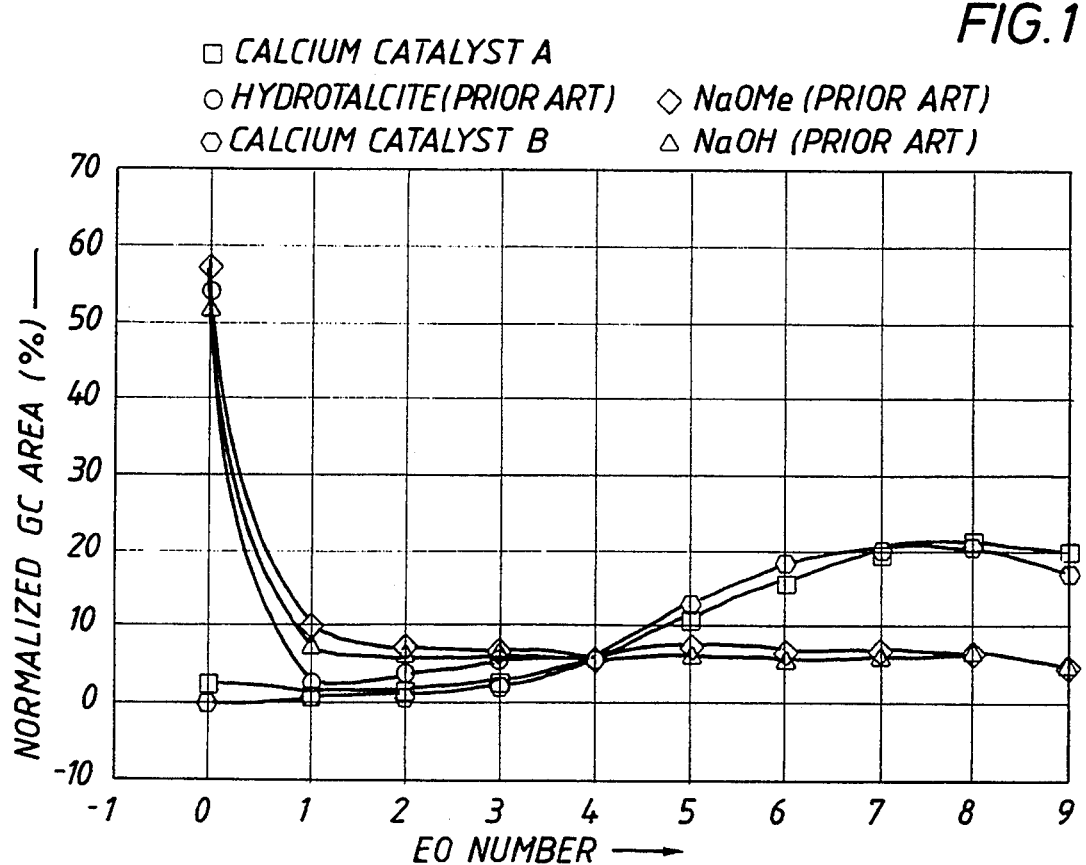
FIG. 1 shows a comparison of alkoxylated methyl esters using the process of the present invention with prior art processes.

In co-pending application Ser. No. 07/748,449, filed Aug. 22, 1991, there is disclosed a process for the production of alkoxylated methyl esters of fatty acids. As disclosed in the aforementioned co-pending application, the alkoxylated methyl esters produced show a sharply peaked distribution of the alkoxylated species. In addition to preparing alkoxylated methyl esters of fatty acids that have such a narrow or peaked distribution of the alkoxylated species, the process disclosed in the aforementioned co-pending application can also be used to prepare alkoxylated diesters and triglycerides, i.e., triesters. In general, the process of the aforementioned co-pending application and the present application is applicable to the alkoxylation of any compound possessing an ester linkage wherein the alkoxylated species is inserted into the starting material ester compound to the desired degree. Accordingly, the term "ester" is intended to include monoesters, diesters and triglycerides as more fully defined herein.

Alkoxylated esters that are produced according to the process of the present invention include alkoxylated monoesters having the formula:

(I)

alkoxylated ethylene glycol diesters having the formula:

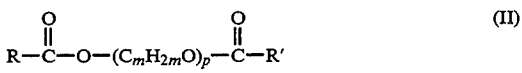
(II)

and alkoxylated triesters having the formula:

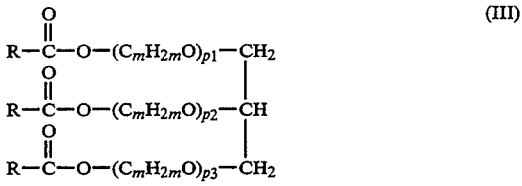
(III)

wherein m is from 2 to 4, $p_1$, $p_2$ and $p_3$ are each from about 1 to about 50, and R and R' are each organic radicals containing from about 1 to about 30 carbon atoms. Especially preferred are esters wherein R is from about 6 to about 30, hereinafter defined as "fatty acid esters," m is 2 and p is from about 4 to about 20. Although R and R' are both each preferably a hydrocarbon radical, especially a linear or branched chain alkyl group, R and R' can also be alkenyl, alkynl, aryl, alkylaryl or alicyclic in nature. R and R' can also contain hetero atoms such as oxygen, sulfur, nitrogen, etc. For example, R and R' can contain ether linkages, ketonic structures, various sulfur containing groups, etc. It is only necessary that R and R' be free of groups containing active hydrogen atoms which would readily alkoxylate or in some other manner deleteriously affect alkoxylation of the ester. Preferably, R and R' will be a branched or straight chain hydrocarbon radical, i.e., an alkyl group, straight chain or linear hydrocarbon radicals being particularly preferred for most surfactant applications. An especially desirable group of alkoxylated esters are those alkoxylated monoesters wherein R' is methyl and R is a branched or straight chain hydrocarbon radical, i.e., an alkyl group having from about 6 to about 30 carbon atoms, especially from about 6 to about 20 carbons atoms.

As noted, the alkoxylated esters produced by the process of the present invention can vary widely in structure and, accordingly, a wide variety of starting, non-alkoxylated esters can be employed. In general, the starting ester will be an alkoxylated monoester having the formula:

$$R-\overset{O}{\underset{\|}{C}}-O-R' \quad \text{(IV)}$$

an ethylene glycol diester having the formula:

$$R-\overset{O}{\underset{\|}{C}}-O-(CH_2)_2-O-\overset{O}{\underset{\|}{C}}-R' \quad \text{(V)}$$

or a triester having the formula:

$$\begin{array}{l} R-\overset{O}{\underset{\|}{C}}-O-CH_2 \\ R-\overset{O}{\underset{\|}{C}}-O-CH \\ R-\overset{O}{\underset{\|}{C}}-O-CH_2 \end{array} \quad \text{(VI)}$$

respectively, depending on the desired end product, and wherein R and R' have the same connotation stated above with respect to Formula I. Non-limiting examples of suitable esters than can be used as starting materials include: the methyl esters of acids such as acetic acid, butyric acid, isobutyric acid, valeric acid, caproic acid, lauric acid, myristic acid, palmitic acid, stearic acid, oleic acid, eicosanoic acid, tricosanoic acid, etc; the ethyl, propyl, butyl, decyl, etc., esters of acids such as acetic acid, butyric acid, isobutyric acid, valeric acid, caproic acid, lauric acid, myristic acid, palmitic acid, stearic acid, oleic acid, eicosanoic acid, tricosoanoic acid, etc., ethylene glycol diesters, such as ethylene glycol diacetate, ethylene glycol dibutyrate, ethylene glycol dihexanoate, ethylene glycol dioctanoate, ethylene glycol didecanoate, ethylene glycol distearate, etc., and triglycerides such as tributyrin, trilaurin, tristearin, etc. In general, the starting ester can be of a type such that (a) the organic radical R contains a relatively few number of carbon atoms, e.g., 3 to 5, and R' is methyl, (b) the organic radical R contains a relatively large number of carbon atoms, e.g., 8 to 30, and R' is methyl, (c) the organic radical R contains a relatively few number of carbon atoms, e.g., 3 to 5, and the organic radical R' contains a relatively large number of carbon atoms, e.g., 8 to 30, (d) the organic radical R contains a relatively large number of carbon atoms, e.g., 8 to 30, and the organic radical R' contains a relatively small number of carbon atoms, e.g., 2 to 6, (e) the organic radicals R and R' both contain relatively few carbon atoms, (f) the organic radical R and R' both contain a relatively large number of carbon atoms, or (g) various combinations of (a)–(f).

The starting material esters may be obtained synthetically or, more conveniently and generally more economically, from natural sources. It is well known, for example, that methyl esters can be made from many triglycerides which are widely distributed in nature in a variety of animal and vegetable products. For example, the ester starting material can be derived from materials such as whale oil, beeswax, carnauba wax, animal fat, etc. Other suitable esters can be derived from vegetable sources such as palm oil, coconut oil, olive oil, cottonseed oil, soybean oil, peanut oil, etc. When obtaining the starting material esters from natural sources, this can be conveniently done by methanolysis followed by stripping or distillation techniques well known to those skilled in the art. It will also be understood that in such cases, a blend of starting material esters is commonly obtained. For example, whereas a stripped methyl coconate will contain mainly $C_{12}$ and $C_{14}$ methyl esters (following methanolysis), an unstripped blend, in addition to such esters also contains appreciable amounts of $C_8$ and $C_{10}$ methyl esters (following methanolysis). In practice, the starting material esters will usually be blends of esters which have been obtained from natural or synthetic sources. Preferred ester starting materials are those esters in which R is a linear or branched chain alkyl group containing from about 6 to 30 carbon atoms, more particularly from 6 to about 20 carbon atoms, and R' is a linear or branched chain alkyl group containing from 1 to 20 carbon atoms, especially from 1 to 10 carbon atoms, particularly preferred being such esters wherein R' is methyl.

The starting material esters are reacted with an alkylene oxide containing from 2 to 4 carbon atoms. Thus, alkylene oxides such as ethylene oxide, propylene oxide, butylene oxide, trimethylene oxide, etc., can be used. It will be understood that mixtures of such alkylene oxides, e.g. mixtures of ethylene oxide and propylene oxide can be employed. Thus, it will be appreciated that the alkoxylated ester can contain an oxyalkylene chain which is heteric in nature (when a single alkylene oxide is used), block in nature (when two or more alkylene oxides are employed) or random in nature (when two or more alkylene oxides are employed). In general, the amount of alkylene oxide used will be such as to provide an alkylene oxide content of from about 10 to about 70 percent-by-weight of the alkoxylated ester. It will be appreciated that the amount of the alkylene oxide employed can be varied over wide limits to tailor the end products for desired purposes. For example, in certain applications it is more desirable that the average number of alkoxy groups per ester molecule be a relatively low number, e.g. from about 2 to about 4, whereas in other applications it is desirable that the number of alkoxy groups be greater, e.g. from about 6 to about 10.

The catalysts used in the process of the present invention are calcium based catalysts, i.e., derived from calcium compounds. The two types of calcium catalysts used in the process of the present invention, identified as Calcium Catalyst A and Calcium Catalyst B, can be prepared by methods well known in the art. Calcium Catalyst A can be produced by the process disclosed in U.S. Pat. No. 4,775,653, incorporated herein by reference for all purposes. Calcium Catalyst B can be prepared by the method disclosed in U.S. Pat. No. 4,820,673, incorporated herein by reference for all purposes.

Since the method of preparing Calcium Catalyst A is clearly taught in U.S. Pat. No. 4,775,653, it need not be discussed in detail herein. However, in general, Calcium Catalyst A is prepared by forming a catalyst pre-mix by admixing and reacting an alkoxylated alcohol mixture containing an alkoxylated alcohol having the general formula:

$$R_1-O-(C_mH_{2m}O)_pH \quad \text{(VII)}$$

wherein $R_1$ is an organic radical containing from about 1 to about 30 carbon atoms, a calcium-containing compound which is at least partially dispersible in the alkoxylated alcohol mixture, an inorganic acid and a metal alkoxide of a Lewis acidic metal such as aluminum titanium, vanadium, etc. Especially preferred are metal alkoxides selected from compounds having the formula:

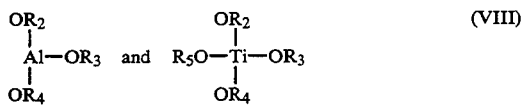

wherein $R_2$, $R_3$, $R_4$ and $R_5$ is each a hydrocarbon radical containing from about 1 to about 30, preferably from about 8 to about 14, carbon atoms, the calcium-containing compound and the alkoxylated alcohol mixture being mixed prior to addition of the metal alkoxide and heating the catalyst pre-mix to a temperature and for a time sufficient to effect at least a partial exchange reaction between the alkoxide groups of the metal alkoxide and the hydroxyl groups of the alkoxylated alcohol. While the use of titanium alkoxides is not disclosed in U.S. Pat. No. 4,775,653, in preparing Calcium Catalyst A, the titanium alkoxide is merely substituted for the aluminum alkoxide or, if desired, a mixture of the aluminum alkoxide and titanium alkoxide can be employed.

In a similar vein, since the preparation of Calcium Catalyst B is clearly taught in U.S. Pat. No. 4,820,673, it is unnecessary to provide a detailed description of its preparation herein. However, in general, Calcium Catalyst B is formed by solubilizing, at least partially, a calcium-containing compound with an activator having the formula:

wherein X and Y are the same or different electronegative, hetero-atoms selected from the group consisting of oxygen, nitrogen, sulfur and phosphorus, a and b are the same or different integers satisfying the valency requirements of X and Y, Q is an organic radical which is electropositive or essentially neutral relative as to X and/or Y, and Z and Z' are the same or different and are either hydrogen or an organic radical which does not prevent said solubilizing. In addition to using either Calcium Catalyst A or Calcium Catalyst B, mixtures of Calcium Catalyst A and Calcium Catalyst B can be employed.

While both calcium catalysts give peaked alkoxylated esters according to the process of the present invention, the use of Calcium Catalyst A is especially preferred since it provides for a much more efficient process to alkoxylate the esters. In particular, Calcium Catalyst A is superior to Calcium Catalyst B with respect to reaction time.

Although as disclosed in U.S. Pat. Nos. 4,775,653 and 4,820,673, Calcium Catalyst A and Calcium Catalyst B, respectively, can be used to alkoxylate compounds having an active hydrogen, e.g. an alcohol, to provide a highly peaked end product, it was unexpected that the calcium-based catalysts would effectively, especially in the case of Calcium Catalyst A, alkoxylate esters which do not possess an active hydrogen.

The alkoxylated esters of the present invention are prepared by reacting a suitable ester starting material, a suitable alkylene oxide(s) in the presence of a catalytically effective amount of Calcium Catalyst A or Calcium Catalyst B. In the case of Calcium Catalyst A, the amount of catalyst employed will generally be from about 0.1 to about 20 weight percent based upon the total reaction mixture. For example, if the weight of the reaction mixture, including all alkylene oxide, is 300 g, typically from about 0.3 g to about 60 g of Calcium Catalyst A would be employed in the reaction. In the case of Calcium Catalyst B, and since Calcium Catalyst B is a less efficient catalytic species, the amount of Calcium Catalyst B employed will range from about 3 to about 90 percent of the total reaction mixture.

The process of the present invention can be conducted over a wide range of temperature and pressure conditions. For example, the reaction can be conducted at temperatures ranging from about 80° C. or lower to about 200° C. and higher. Pressures can range from sub ambient up to about 100 psi, pressures of from about 10 to about 60 psi being preferred.

Typically, the process can be conducted by charging a suitable reaction vessel, e.g. an autoclave, with the ester starting material in the desired amount. In this regard, the amount of ester starting material chosen will be determined by the desired weight percent of the alkylene oxide in the final alkoxylated ester product. The mixture is then heated to the desired elevated temperature under nitrogen or some other suitable inert gas. The reactor is then placed under vacuum to produce a nitrogen sparge in the reactor to remove water, if present. The catalyst is then injected into the reaction mixture and the temperature raised to the desired reaction temperature, the reaction mixture being maintained under a nitrogen blanket. When the desired reaction temperature is reached, the reactor is evacuated and the chosen alkylene oxide, e.g. ethylene oxide, introduced at the appropriate pressure. As the alkylene oxide reacts, additional amounts are added, the temperature being maintained substantially constant throughout the reaction.

In a modified process to prepare alkoxylated esters of the present invention, a two-step, one-pot approach can be employed. In this method, an alcohol containing the R' group is reacted with the alkylene oxide using from about 0.1 to about 20 percent-by-weight (based on final reaction mixture weigh) of the calcium based catalyst, the temperature ranging from 50° to 200° C., the pressure ranging from sub-ambient to 100 psi or higher. This results in the formation of an alkoxylated alcohol containing the R' group. It will be apparent that the amount of alcohol and alkylene oxide chosen will be determined by the desired weight percent of the alkylene oxide in the final alkoxylated ester product. After the alkoxylated alcohol has been formed, it can then be transesterified in the same vessel that the alkoxylation of the alcohol occurred and containing the calcium-based catalyst, the alkoxylated alcohol being reacted with, for example, the methyl ester of an ester containing the R group to thereby produce the alkoxylated ester of Formula I, preferably with continuous removal of methanol. The two-step, one-pot process takes place according to the following equations:

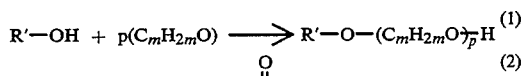
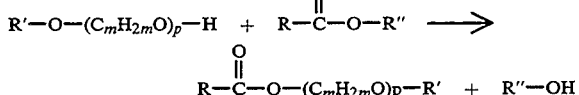
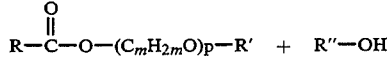

In this method, the ester containing the R' group can be added to the vessel together with the alcohol being ethoxylated or it can be added after the ethoxylation step.

The alkoxylated esters produced by the process of the present invention find utility as detergents, surfactants and the like.

Certain of the alkoxylated methyl esters and ethylene glycol diesters of the present invention, as distinguished from prior art methyl alkoxylated esters of that type, are markedly "peaked" providing new compositions. The unique, peaked alkoxylated methyl esters and diesters of the present invention are characterized by a distribution such that, when the most prevalent alkoxylated species has greater than about 5 oxyalkylene groups per ester linkage, the portion of the product mixture having 3 or more oxyalkylene groups per ester linkage than the most prevalent alkoxylation species is less than 50 percent-by-weight of the mixture. Similarly, in this case the alkoxylation species having fewer oxyalkylene groups per ester linkage by 3 or more oxyalkylene groups than the most prevalent alkoxylation species is usually relatively minor, e.g. less than about 25 percent-by-weight, more often less than about 15 percent-by-weight of the product mixture. Thus, there is produced a new composition of matter comprising a compound selected from the group consisting of alkoxylated methyl esters having the formula:

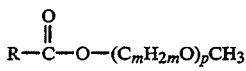 (X)

$$R-C(=O)-O-(C_mH_{2m}O)_p CH_3$$

and alkoxylated ethylene glycol diesters having the formula:

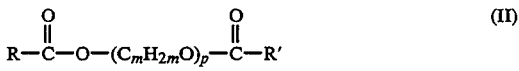 (II)

$$R-C(=O)-O-(C_mH_{2m}O)_p-C(=O)-R'$$

wherein m is from 2 to 4, p is from about 6 to about 11 and R is an organic radical containing from about 1 to about 30 carbon atoms, the alkoxylated ester composition comprising a mixture having a molecular weight distribution such that the portion of the mixture having 3 or more oxyalkylene groups per ester linkage than the most prevalent alkoxylation species is less than 50 percent-by-weight of the mixture and the portion of the mixture having fewer oxyalkylene groups per ester linkage by 3 or more oxyalkylene groups than the most prevalent alkoxylation species is less than about 25 percent-by-weight, more often less than about 15 percent-by-weight.

Although the sharp, unexpected degree of peaking noted with the alkoxylated methyl esters is not seen in the case of alkoxylated monoesters wherein R' contains 2 or more carbon atoms (so-called "fatty-fatty esters"), or in the case of the alkoxylated triglycerides, nonetheless certain of the monoesters wherein R' contains 2 or greater carbon atoms exhibit significant peaking as compared with such compounds produced by prior art processes and as determined by analytical data. It will be appreciated that one of the problems of determining peaking in the case of monoesters of Formula I wherein R' contains 2 or more carbon atoms, and in the case of the triglycerides, is the difficulty of analyzing relatively high molecular-weight, complex molecules. In general, it can be stated that the alkoxylated monoesters of Formula I wherein R' is not methyl, as distinguished from prior art alkoxylated monoesters, are "peaked." Such peaked alkoxylated monoesters are characterized by a distribution such that they have a narrower band range of the alkoxylation species.

In the process of the present invention, particularly employing Calcium Catalyst A, it is possible to produce alkoxylated methyl esters that exhibit peaking at two different levels of alkoxylation, i.e., one can not only obtain, as shown in DE 3914131, a relatively narrow homolog distribution of the alkoxylated ester wherein the product has an average of from about 1 to about 5 oxyalkylene groups per ester linkage; it is also possible, as noted above, to obtain a markedly narrow homolog distribution of the alkoxylated methyl ester wherein the product has an average of from about 6 to about 9 oxyalkylene groups per ester linkage. In the latter case it is found that the composition of the present invention exhibits unexpected peaking in the sense that products made by prior art processes using catalysts such as NaOH, NaOMe or hydrotalcite exhibit very little to slight peaking in the range of oxyalkylene groups per ester linkage. By adjusting conditions, e.g. concentration of reactants, one can peak the alkoxylated methyl ester around virtually any desired homolog.

To more fully illustrate the present invention, the following non-limiting examples are presented.

ALKOXYLATION OF METHYL ESTERS

EXAMPLE 1

A series of experiments were conducted to demonstrate the preparation of alkoxylated methyl esters using the process of the present invention as well as prior art processes for comparative purposes to show that the process of the present invention is much more efficient in requiring less catalyst, or exhibiting shorter reaction times or higher conversion rates or in resulting in an alkoxylated methyl ester which shows significantly greater peaking than that obtained by prior art processes and catalysts.

Procedure 1—Typical Preparation of Ethoxylated Methyl Ester Using NaOMe Catalyst A stainless steel autoclave is charged with the requisite amount of the starting material ester as determined by the desired weight percent ethylene oxide in the final product and the desired amount of NaOMe. For example, in a typical preparation, if the total final reaction mixture is 300 g, 1.0 g of NaOMe, i.e., 0.3 weight percent based on the total final weight of reaction mixture, is used. The mixture is heated under nitrogen to 110° C. at which time a vacuum is applied to produce a nitrogen sparge of 5 psig in the reactor. The reaction mixture is sufficiently dry after 20 minutes of sparging. Optionally, fifteen grams of a co-catalyst such as n-dodecanol or an alcohol ethoxylate (5% based on the weight of the reaction mixture) is injected. The temperature is subsequently raised to 175° C. with nitrogen blanketing the reaction mixture. At 175° C., the reactor is evacuated and ethylene, oxide (EO) introduced to approximately 50 psig. Subsequent amounts of ethylene oxide are introduced into the reactor when the pressure drops as a result of ethoxylation. Temperature is maintained at or near 175° C. throughout the reaction. The catalyst is destroyed .upon completion of the reaction by injection of the requisite amount of glacial acetic acid after cooling to approximately 80° C.

Procedure 2—Typical Preparation of Ethoxylated Methyl Ester Using NaOH Catalyst

The procedure employed using the NaOMe catalyst is employed with the exception that 50 percent-by-weight aqueous sodium hydroxide is employed as a catalyst.

Procedure 3—Typical Preparation of Ethoxylated Methyl Ester Using Calcined Hydrocalcite as the Catalyst The process used in this example corresponds to that disclosed in Example 2 of German reference DE 3914131, incorporated herein by reference for all purposes.

Procedure 4—Typical Preparation of Ethoxylated Methyl Ester Using Calcium Catalyst B The procedure employed was essentially the same as Procedure 1 with the exception that Calcium Catalyst B prepared as per the teachings of Run No. 21 of Example 1 of U.S. Pat. No. 4,820,673 was used and the catalyst was added to the starting material ester after drying. Additionally, no dodecanol or alcohol ethoxylate was employed and the catalyst was not destroyed using glacial acetic acid. In preparing Calcium Catalyst B, a three neck flask equipped with mechanical stirrer, nitrogen purge and a condenser for vacuum distillation was employed. Nine grams of CaO and 840 grams of MEEG (monoethyl ether of ethylene glycol) were introduced into the flask. The mixture was heated to 135°–140° C. with removal of water and some MEEG over a period of about 5 hours. ALFOL ® 1214 GC alcohol, 890 g, (trademark of a blend of 30% w/w 12 carbon and 70% w/w 14 carbon alcohols marketed by Vista Chemical Company) was then introduced and the reaction mixture cooled to 75° C. Concentrated $H_2SO_4$, 3.05 g, was added. Distillation of MEEG followed upon heating to 175°–180° C. The majority of the MEEG was removed at this stage. Some loss of alcohol was compensated by the addition of 300 g more of ALFOL ® 1214 GC alcohol. The residual MEEG was removed from the reaction mixture at 225° C. and about 180 mm Hg. Final GC traces of the reaction mixture showed no MEEG present. Enough ALFOL ® 12 (trademark of n-dodecanol marketed by Vista Chemical Company) was subsequently added to the catalyst to reestablish the $C_{12}$ to $C_{14}$ alcohol ratios observed in ALFOL ® 1214 GC alcohol. The Calcium Catalyst B employed had a Ca:SO_4 ratio of 5.2:1 derived from calcium oxide and sulfuric acid. The catalyst contained 0.096 g of calcium, i.e., 0.96 percent-by-weight calcium, corresponding to 10.0 g of catalyst for reaction.

Procedure 5—Typical Preparation of Ethoxylated Methyl Ester Using Calcium Catalyst A The procedure employed was the same as Procedure 4 with the exception that Calcium Catalyst A prepared substantially as per the teachings of U.S. Pat. No. 4,775,653 was employed and there was no addition of n-dodecanol or alcohol ethoxylate. Additionally, it was not necessary to destroy the catalyst by the addition of glacial acetic acid. To prepare Calcium Catalyst A, in general a mixture of 125 g ALFONIC ® 1012-40[1] alcohol ethoxylate, 2 g 2-ethyl hexanoic acid, and 10.9 g Ca(OH)$_2$ was stirred in a stainless steel autoclave under a nitrogen atmosphere while concentrated $H_2SO_4$ (2 g) was added over a period of 10 minutes. Stirring was continued after $H_2SO_4$ addition for about 5 hours. The mixture was subsequently heated to 150° C. and sparged for 15 minutes with nitrogen to remove water. Upon cooling to about 125° C., 17.5 g of aluminum trialkoxide in which the alkoxide groups have an average chain length of 10 carbon atoms (mixed 2–30 carbon chain length) and containing about 6 percent-by-weight of aluminum was added, the mixture being maintained under nitrogen. The temperature was then raised to 190° C. at which time stripping of a portion of the alcohol from the aluminum alkoxide took place using a nitrogen sparge. Heating at 190° C. for an additional 0.5 hour followed by cooling under nitrogen to ambient temperature provided the active catalyst. The Calcium Catalyst A employed had a Ca:SO$_4$:Al ratio of 5:1:1 derived from calcium hydroxide, sulfuric acid and aluminum. The combined amount of Ca and Al in the catalyst was 0.054 g, i.e., the catalyst contained 3 percent-by-weight calcium and 0.6 percent-by-weight aluminum.

[1]Mixture of 52.8 percent-by-weight $C_{10}$ alcohol and 4.2 percent-by-weight $C_{12}$ alcohol with 40 percent-by-weight ethylene oxide marketed by Vista Chemical Company.

Table 1 below shows the data obtained on a series of ethoxylated methyl esters made according to the process of the present invention using Procedure 5, i.e., employing Calcium Catalyst A as compared with a run using Procedure 1 (NaOMe catalyst). In Table 1 and the other Tables, the "Target" refers to the desired weight percent ethoxylates. Also, in all cases "final reaction mixture" means the combined weight of the starting material ester and the alkylene (ethylene) oxide.

TABLE 1

METHYL ESTER ETHOXYLATES:
DATA FOR CALCIUM CATALYST A[a] (CCA) AND NaOMe

| Expt. No. | Me Ester | EO % w/w Target | EO % w/w Calc.[b] | Obsd.[c] | Catalyst | Cat. g | Run Time min. |
|---|---|---|---|---|---|---|---|
| 1 | myristate | 60 | 61.2 | 61.5 | CCA | 3.0[a] | 91[d] |
| 2 | myristate | 60 | 60.2 | | CCA | 6.0[a] | 55[e] |
| 3 | myristate | 60 | | 60.0 | CCA | 3.0[a] | 60[f] |
| 4 | myristate | 60 | 59.5 | | CCA | 9.0[a] | 48 |
| 5 | coconate[g] | 55 | 53.3 | 61.0 | CCA | 1.5[h] | 115 |
| 6 | coconate[g] | 60 | 60.5 | 64.1 | CCA | 3.0[a] | 146 |
| 7 | coconate[g] | 65 | 63.4 | 71.3 | CCA | 1.5[h] | 106 |
| 8 | coconate[g] | 70 | 68.9 | 73.9 | CCA | 1.5[h] | 105 |
| 9 | coconate[i] | 55 | 54.7 | 59.1 | CCA | 1.5[h] | 59 |
| 10 | coconate[i] | 60 | 60.5 | 63.5 | CCA | 3.0[a] | 84 |
| 11 | coconate[i] | 65 | 64.4 | 68.8 | CCA | 1.5[h] | 57 |
| 12 | coconate[i] | 70 | 70.5 | 75.5 | CCA | 1.5[h] | 70 |
| 13 | myristate[j] | 60 | 60.9 | 61.4 | CCA | 3.0[a] | 84 |
| 14 | laurate | 30 | 28.8 | 33.0 | CCA | 1.5[h] | 44 |

TABLE 1-continued

METHYL ESTER ETHOXYLATES:
DATA FOR CALCIUM CATALYST $A^a$ (CCA) AND NaOMe

| Expt. No. | Me Ester | Target | EO % w/w Calc.[b] | Obsd.[c] | Catalyst | Cat. g | Run Time min. |
|---|---|---|---|---|---|---|---|
| 15 | laurate | 30 | 29.3 | 27.6 | NaOMe[k] | 0.75[h] | 101 |

[a] For each experiment, the total final reaction mixture weight was 300 g and the reaction temperature was 175° C., unless specified otherwise.
[b] Calculated from weight of final reaction mixture.
[c] These values obtained by nuclear magnetic resonance spectroscopy.
[d] 8.4 ppm dioxane in final reaction mixture.
[e] 7.1 ppm dioxane in final reaction mixture.
[f] 115° C. reaction temperature; the only products were polyethylene glycol and recovered starting material.
[g] Unstripped methyl coconate, mainly $C_{12}$ and $C_{14}$ methyl esters with some $C_8$ and $C_{10}$ methyl esters.
[h] For this experiment, the total final reaction mixture weight was 150 g.
[i] Stripped methyl coconate, mainly $C_{12}$ and $C_{14}$ methyl esters.
[j] Repeat of Experiment No. 1.
[k] Crystalline solid.

As can be seen from the data in Table 1, the use of Calcium Catalyst A is markedly better in terms of catalyst used than the use of a conventional sodium methoxide catalyst. For example, in comparing Experiments Nos. 14 and 15, the combined weight of calcium and aluminum in Calcium Catalyst A used in Experiment No. 14 is 0.054 g, whereas the amount of sodium employed in Experiment No. 15 is 0.32 g. Note also that for the same target amount of ethoxylation, there is a marked difference in run time between Experiment No. 14 using Calcium Catalyst A and Experiment No. 15 using the sodium methoxide catalyst.

Table 2 below shows comparative examples on the use of Calcium Catalyst A (Procedure 5) versus the use of other catalysts for producing low-mole ethylene oxide adducts of various methyl esters.

TABLE 2

COMPARATIVE EXAMPLES:
USE OF $CCA^a$ VS. OTHER CATALYSTS FOR LOW-MOLE EO ADDUCTS

| Expt. No. | Me Ester | Target | EO % w/w Calc.[b] | obsd.[c] | Catalyst | Cat. g | EO No.[d] | GC Area %[e] | Run Time min. |
|---|---|---|---|---|---|---|---|---|---|
| 14 | laurate | 30 | 28.8 | 33.0 | CCA | 1.5 | 0 | 28.7 | 44 |
|  |  |  |  |  |  |  | 1 | 8.4 |  |
|  |  |  |  |  |  |  | 2 | 14.1 |  |
|  |  |  |  |  |  |  | 3 | 15.6 |  |
|  |  |  |  |  |  |  | 4 | 13.6 |  |
|  |  |  |  |  |  |  | 5 | 11.1 |  |
|  |  |  |  |  |  |  | 6 | 8.5 |  |
| DE[f] | laurate | 30 | g | g | HT[h] | i | 0 | 35.0 | 45 |
|  |  |  |  |  |  |  | 1 | 13.5 |  |
|  |  |  |  |  |  |  | 2 | 15.8 |  |
|  |  |  |  |  |  |  | 3 | 13.6 |  |
|  |  |  |  |  |  |  | 4 | 10.7 |  |
|  |  |  |  |  |  |  | 5 | 6.5 |  |
|  |  |  |  |  |  |  | 6 | 4.8 |  |
| j | laurate | 30 | g | g | NaOMe[k] | i | 0 | 67.6 | g |
|  |  |  |  |  |  |  | 1 | 12.6 |  |
|  |  |  |  |  |  |  | 2 | 4.7 |  |
|  |  |  |  |  |  |  | 3 | 3.7 |  |
|  |  |  |  |  |  |  | 4 | 3.4 |  |
|  |  |  |  |  |  |  | 5 | 4.7 |  |
|  |  |  |  |  |  |  | 6 | 3.2 |  |
| 15 | laurate | 30 | 29.3 | 27.6 | NaOMe[k] | 0.75[l] | 0 | 72.0 | 101 |
|  |  |  |  |  |  |  | 1 | 6.4 |  |
|  |  |  |  |  |  |  | 2 | 4.2 |  |
|  |  |  |  |  |  |  | 3 | 4.3 |  |
|  |  |  |  |  |  |  | 4 | 4.2 |  |
|  |  |  |  |  |  |  | 5 | 4.9 |  |
|  |  |  |  |  |  |  | 6 | 3.7 |  |

[a] The total final reaction mixture weight was 150 g and the reaction temperature was 175° C. Amount of catalyst used was 1.0% w/w based on weight of final reaction mixture.
[b] Calculated from weight of final reaction mixture.
[c] These values obtained by nuclear magnetic resonance spectroscopy.
[d] Number of EO moieties per methyl laurate molecule; 0 represents unreacted starting material.
[e] Normalizd area %; calculated from either gas chromatographic data or German Patent DE 3914131 AI (HT d NAOM, catalysts).
[f] German Patent DE 3914131 Al; data in the table were taken from this patent.
[g] Data not available.
[h] Calcined hydrotalcite.
[i] Number of grams of catalyst not available; amount of catalyst used was 0.5% w/w based on weight of final reaction mixture.
[j] Data for NaOMe catalyst taken from German Patent DE 3914131 A1.
[k] Crystalline solid.
[l] Amount of catalyst used was 0.5% w/w based on a total final reaction mixture weight of 150 g.

As can be seen from the data in Table 2, using the process of Procedure 5 (Calcium Catalyst A), there is a marked increase in conversion as compared with the use of the process of Procedure 3 (calcined hydrotalcite) or the process of Procedure 1 (sodium methoxide). Note for example with respect to Experiment No. 14 that there is only 28.7 percent of unreacted starting material using Calcium Catalyst A as compared with 35 percent of unreacted starting material using calcined hydrotalcite (Experiment No. DE), 67.6 percent unreacted starting material using sodium methoxide (Experiment No. j) or 72 percent unreacted starting material using sodium methoxide (Experiment No. 15). Additionally, far less catalyst (based on active metal content) is required in the case of Experiment No. 14 than in the other experiments shown in Table 2. Note that in Experiment No. DE, the combined weight percent of Al and Mg is about 0.5 percent.

Table 3 shows further comparative examples on ethoxylating methyl esters using the process of Procedure 5 (Calcium Catalyst A) and the process of Procedure 4 (Calcium Catalyst B) as compared with the use of the process of Procedure 3 (hydrotalcite catalyst), the process of Procedure 1 (sodium methoxide catalyst), or the process of Procedure 2 (sodium hydroxide catalyst).

TABLE 3

COMPARATIVE EXAMPLES: USE OF CCA[a] AND CALCIUM CATALYST B (CCB[i]) VS. USE OF OTHER CATALYSTS FOR HIGH-MOLE EO ADDUCTS

| Expt. No. | Me Ester | Target | EO % w/w Calc.[b] | Obsd.[c] | Catalyst | Cat. q | EO No.[d] | GC Area %[e] | Run Time min. |
|---|---|---|---|---|---|---|---|---|---|
| 1[a] | myristate | 60 | 61.2 | 61.5 | CCA | 3.0 | 0 | 2.5 | 91 |
| | | | | | | | 1 | 1.2 | |
| | | | | | | | 2 | 1.5 | |
| | | | | | | | 3 | 3.1 | |
| | | | | | | | 4 | 6.0 | |
| | | | | | | | 5 | 10.4 | |
| | | | | | | | 6 | 15.5 | |
| | | | | | | | 7 | 19.9 | |
| | | | | | | | 8 | 20.8 | |
| | | | | | | | 9 | 19.2 | |
| 16[f] | myristate | 60 | 61.2 | 61.7 | HT[g] | 1.5 | 0 | 53.8 | 215 |
| | | | | | | | 1 | 2.6 | |
| | | | | | | | 2 | 4.1 | |
| | | | | | | | 3 | 4.8 | |
| | | | | | | | 4 | 5.3 | |
| | | | | | | | 5 | 5.9 | |
| | | | | | | | 6 | 6.4 | |
| | | | | | | | 7 | 6.5 | |
| | | | | | | | 8 | 6.2 | |
| | | | | | | | 9 | 4.5 | |
| 17[h] | myristate | 60 | 58.1 | 58.8 | CCB | 10.0 | 0 | 0.3 | 1076 |
| | | | | | | | 1 | 0.8 | |
| | | | | | | | 2 | 0.8 | |
| | | | | | | | 3 | 2.8 | |
| | | | | | | | 4 | 7.0 | |
| | | | | | | | 5 | 12.8 | |
| | | | | | | | 6 | 18.0 | |
| | | | | | | | 7 | 20.4 | |
| | | | | | | | 8 | 20.3 | |
| | | | | | | | 9 | 16.8 | |
| 18[j] | myristate | 60 | 57.9 | 58.6 | NaOMe[k] | 1.0 | 0 | 57.1 | 450 |
| | | | | | | | 1 | 9.9 | |
| | | | | | | | 2 | 7.5 | |
| | | | | | | | 3 | 7.4 | |
| | | | | | | | 4 | 5.9 | |
| | | | | | | | 5 | 7.0 | |
| | | | | | | | 6 | 5.2 | |
| 19[l] | myristate | 60 | 57.1 | 59.3 | NAOH[m] | 1.5 | 0 | 51.5 | 353 |
| | | | | | | | 1 | 7.2 | |
| | | | | | | | 2 | 6.1 | |
| | | | | | | | 3 | 6.5 | |
| | | | | | | | 4 | 5.7 | |
| | | | | | | | 5 | 5.5 | |
| | | | | | | | 6 | 5.6 | |
| | | | | | | | 7 | 5.8 | |
| | | | | | | | 8 | 6.2 | |

[a]The total final reaction mixture weight was 300 g and the reaction temperature was 175° C. Amount of CCA catalyst used was 1.0% w/w based on weight of final reaction mixture. No alcohol or alcohol ethoxylate cocatalyst was used.
[b]Calculated from weight of final reaction mixture.
[c]These values obtained by nuclear magnetic resonance spectroscopy.
[d]Number of EO moieties per methyl myristate molecule; 0 represents unreacted starting material.
[e]Normalizd area %; calculated from gas chromatographic data.
[f]German Patent DE 3914131 A1; the total final reaction mixture weight was 300 g and the reaction temperature was 175° C. No alcohol or alcohol ethoxylate cocatalyst was used. Amount of calcined hydrotalcite catalyst used was 0.5% w/w based on weight of final reaction mixture.
[g]Calcined hydrotalcite; prepared according to Patent DE 3914131 A1.
[h]Calcium Catalyst B as per U.S. Pat. No. 4,820,673; the total final reaction mixture weight was 300 g and the reaction temperature was 175° C. Amount of CaO-based catalyst used was 3.3% w/w based on weight of final reaction mixture. No alcohol or alcohol ethoxylate cocatalyst was used.
[i]CaO-based catalyst; prepared according to U.S. Pat. No. 4,820,673.
[j]In this process, the total final reaction mixture weight was 300 g and the reaction temperature was 175° C. ALFOL[1] ® (n-dodecanol) alcohol cocatalyst was used (15.0 g, 5.0% w/w based on weight of final reaction mixture). Amount of NaOMe catalyst used was 0.3% w/w based on weight of final reaction mixture.
[k]Crystalline solid.
[l]In this process the total final reaction mixture weight was 300 g and the reaction temperature was 175° C. ALFOLO ® (n-dodecmol) alcohol cocatalyst was used (15.0 g, 5.0% w/w based on weight of final reaction mixture). Amount of NaOH catalyst used 0.5% w/w based on weight of final reaction mixture.
[m]50% aqueous solution.
[1]Trademark of Vista Chemical Company As can be seen from the data in Table 3, and with respect to high-mole ethylene oxide adducts of the methyl esters, reaction times are greatly reduced using the process employing Calcium Catalyst A as opposed to processes that use sodium methoxide, sodium hydroxide or hydrotalcite. With respect to both Calcium Catalyst A and Calcium Catalyst B, conversion rates are much higher (note the small amount of unreacted starting material in Experiments 1 and 17 as compared with Experiments 16, 18 and 19). Lastly, use of calcium-based catalysts such as Calcium Catalyst A or Calcium Catalyst B results in an ethoxylated methyl ester which shows greatly enhanced peaking relative to the other catalyst systems employed. The data in Table 3 are graphically demonstrated in FIG. 1 which shows that the most prevalent EO species, i.e., about 8 in the case of Calcium Catalyst A and about 7 in the case of Calcium Catalyst B is greater than 20 percent. This is to be contrasted with the products obtained using the other processes which show virtually no peaking in that range of ethylene oxide adducts.

Table 4 below gives a comparison of reaction time profiles using processes employing Calcium Catalyst A, Calcium Catalyst B, hydrotalcite, sodium methoxide and sodium hydroxide.

TABLE 4

COMPARATIVE EXAMPLES: REACTION TIME PROFILES USING VARIOUS CATALYSTS FOR HIGH-MOLE EO ADDUCTS

| Expt. No. | Me Ester | Target | EO % w/w Calc.[b] | Obsd.[c] | Catalyst | Cat. g | Reaction Time (min.) | EO Reacted (g)[d] |
|---|---|---|---|---|---|---|---|---|
| 1[a] | myristate | 60 | 61.2 | 61.5 | CCA | 3.0 | 0 | 0.0 |
| | | | | | | | 1 | 9.0 |
| | | | | | | | 16 | 23.2 |
| | | | | | | | 31 | 45.0 |
| | | | | | | | 46 | 77.2 |
| | | | | | | | 61 | 110.6 |
| | | | | | | | 76 | 146.6 |
| | | | | | | | 91 | 180.0 |
| 16[e] | myristate | 60 | 61.2 | 61.7 | HT[f] | 1.5 | 0 | 0.0 |
| | | | | | | | 3 | 14.2 |
| | | | | | | | 8 | 19.3 |
| | | | | | | | 18 | 32.2 |
| | | | | | | | 28 | 43.7 |
| | | | | | | | 38 | 51.4 |
| | | | | | | | 48 | 61.7 |
| | | | | | | | 50 | 64.3 |
| | | | | | | | 58 | 70.7 |
| | | | | | | | 68 | 80.4 |
| | | | | | | | 78 | 88.1 |
| | | | | | | | 88 | 96.4 |
| | | | | | | | 98 | 103.5 |
| | | | | | | | 118 | 117.0 |
| | | | | | | | 138 | 132.5 |
| | | | | | | | 168 | 153.0 |
| | | | | | | | 198 | 172.3 |
| | | | | | | | 215 | 180.0 |
| 17[g] | myristate | 60 | 58.1 | 58.8 | CCB[h] | 10.0 | 0 | 0.0 |
| | | | | | | | 2 | 10.3 |
| | | | | | | | 32 | 12.9 |
| | | | | | | | 69 | 23.2 |
| | | | | | | | 96 | 28.3 |
| | | | | | | | 122 | 33.4 |
| | | | | | | | 152 | 37.3 |
| | | | | | | | 212 | 47.6 |
| | | | | | | | 272 | 56.6 |
| | | | | | | | 336 | 65.6 |
| | | | | | | | 416 | 78.4 |
| | | | | | | | 452 | 83.6 |
| | | | | | | | 812 | 142.8 |
| | | | | | | | 872 | 153.0 |
| | | | | | | | 932 | 162.0 |
| | | | | | | | 992 | 171.0 |
| | | | | | | | 1076 | 180.0 |
| 18[i] | myristate | 60 | 57.9 | 58.6 | NaOMe[j] | 1.0 | 0 | 0.0 |
| | | | | | | | 20 | 9.0 |
| | | | | | | | 30 | 24.4 |
| | | | | | | | 45 | 32.2 |
| | | | | | | | 75 | 54.0 |
| | | | | | | | 105 | 81.0 |
| | | | | | | | 135 | 104.2 |
| | | | | | | | 165 | 120.9 |
| | | | | | | | 334 | 167.2 |
| | | | | | | | 375 | 173.6 |
| | | | | | | | 450 | 180.0 |
| 19[k] | myristate | 60 | 57.1 | 59.3 | NaOH[l] | 1.5 | 0 | 0.0 |
| | | | | | | | 2 | 9.0 |
| | | | | | | | 17 | 9.0 |
| | | | | | | | 42 | 10.3 |
| | | | | | | | 82 | 14.1 |
| | | | | | | | 102 | 23.1 |
| | | | | | | | 117 | 33.4 |
| | | | | | | | 132 | 42.3 |

TABLE 4-continued

COMPARATIVE EXAMPLES: REACTION TIME PROFILES USING VARIOUS CATALYSTS FOR HIGH-MOLE EO ADDUCTS

| Expt. No. | Me Ester | Target | EO % w/w Calc.[b] | Obsd.[c] | Catalyst | Cat. g | Reaction Time (min.) | EO Reacted (g)[d] |
|---|---|---|---|---|---|---|---|---|
| | | | | | | | 147 | 57.9 |
| | | | | | | | 162 | 70.7 |
| | | | | | | | 192 | 95.2 |
| | | | | | | | 229 | 119.6 |
| | | | | | | | 253 | 132.4 |
| | | | | | | | 260 | 137.6 |
| | | | | | | | 302 | 159.5 |
| | | | | | | | 327 | 169.8 |
| | | | | | | | 347 | 176.2 |
| | | | | | | | 353 | 180.0 |

[a] The total final reaction mixture weight was 300 g and the reaction temperature was 175° C. Amount of CCA catalyst used was 1.0% w/w based on weight of final reaction mixture. No alcohol or alcohol ethoxylate cocatalyst was used.
[b] Calculated from weight of final reaction mixture.
[c] These values obtained by nuclear magnetic resonance spectroscopy.
[d] The amount of EO listed as "reacted" within the first 1-2 minutes of the run actually reflects the dead volume of the EO addition line. That is, the dead volume of the EO addition line was 9.0 g (of EO) and this amount, listed as "EO Reacted", actually is the amount of EO needed to liquid-fill the line and, therefore, is not strictly "reacted" EO.
[e] German Patent DE 3914131 AI; die total final reaction mixture weight was 300 g and the reaction temperature was 175° C. Amount of calcined hydrotalcite catalyst used was 0.5% w/w based on weight of final reaction mixture. No alcohol or alcohol ethoxylate cocatalyst was used.
[f] Calcined hydotalcite; prepared according to German Patent DE 3914131 AI.
[g] Calcium Catalyst B as per U.S. Pat. No. 4,820,673; the total final reaction mixture weight was 300 g and the reaction temperature was 175° C. No alcohol or alcohol ethoxylate cocatalyst was used. Amount of CaO-based catalyst used was 3.3% w/w based on weight of final reaction mixture.
[h] CaO-based catalyst; prepared according to U.S. Pat. No. 4,820,673.
[i] In this process, the total final reaction mixture weight was 300 g and the reaction temperature was 175° C. ALFOLO ® 12 (n-dodecanol) alcohol cocatalyst was used (15.0 g, 5.0% w/w based on weight of final reaction mixture). Amount of NaOMe catalyst used was 0.3% w/w based on weight of final reaction mixture.
[j] Crystalline solid.
[k] In this process the total final reaction mixture weight was 300 g and the reaction temperature was 175° C. ALFOL ® 12 (n-dodecanol) alcohol cocatalyst was used (15.0 g, 5.0% w/w based on weight of final reaction mixture). Amount of NaOH catalyst used 0.5% w/w based on weight of final reaction mixture.
[l] 50% iqueous solution.
*Trademark of vista Chemical Company.

As can be seen from the data in Table 4, by using the process of Procedure 5 (Calcium Catalyst A) reaction times are significantly decreased. As also shown from the data in Table 4 as well as the previous tables, the amount of catalyst employed, based on active metal content is markedly less in the case of calcium-based catalysts such as Calcium Catalyst A and Calcium Catalyst B as compared with catalysts such as hydrotalcite, sodium methoxide or sodium hydroxide.

Table 5 below gives the results of a comparison of using Calcium Catalyst A wherein a titanium alkoxide is substituted for aluminum alkoxide. In preparing Calcium Catalyst A using titanium alkoxide, the process of Procedure 5 was followed with the exception that titanium alkoxide was used instead of aluminum alkoxide. Experiment No. 23 in Table 5 also demonstrates that the deletion of 2-ethylhexanoic acid from the process of Procedure 5 makes Calcium Catalyst A less effective vis-a-vis run time and peaking but still gives much higher conversion than processes using NaOH, NaOMe or hydrotalcite as catalysts.

TABLE 5

COMPARISON OF USE OF CCA (Using Aluminum Alkoxide) AND CCA (Using Titanium Alkoxide)

| Expt. No. | Me Ester | Target | EO % w/w Calc.[b] | Obsd.[c] | Catalyst | Cat. g | EO No.[d] | GC Area %[e] | Run Time min. |
|---|---|---|---|---|---|---|---|---|---|
| 14[a] | laurate | 30 | 28.8 | 33.0 | f | 1.5 | 0 | 27.0 | 44 |
| | | | | | | | 1 | 7.9 | |
| | | | | | | | 2 | 13.3 | |
| | | | | | | | 3 | 14.7 | |
| | | | | | | | 4 | 12.8 | |
| | | | | | | | 5 | 10.5 | |
| | | | | | | | 6 | 8.0 | |
| | | | | | | | 7 | 6.0 | |
| 21[a] | laurate | 30 | 25.2 | 25.1 | g | 3.0 | 0 | 51.7 | 65 |
| | | | | | | | 1 | 8.8 | |
| | | | | | | | 2 | 11.4 | |
| | | | | | | | 3 | 9.8 | |
| | | | | | | | 4 | 7.4 | |
| | | | | | | | 5 | 5.3 | |
| | | | | | | | 6 | 3.5 | |
| | | | | | | | 7 | 2.2 | |
| 22[a] | laurate | 30 | 28.3 | 31.3 | h | 3.0 | 0 | 12.8 | 28 |
| | | | | | | | 1 | 3.7 | |
| | | | | | | | 2 | 4.9 | |
| | | | | | | | 3 | 4.6 | |
| | | | | | | | 4 | 4.3 | |
| | | | | | | | 5 | 4.0 | |
| | | | | | | | 6 | 3.6 | |
| | | | | | | | 7 | 3.2 | |
| 23[a] | myristate | 60 | 63.4 | | i | 3.0 | 0 | 9.0 | 83 |

TABLE 5-continued

COMPARISON OF USE OF CCA (Using Aluminum Alkoxide) AND CCA (Using Titanium Alkoxide)

| Expt. No. | Me Ester | Target | EO % w/w Calc.[b] | Obsd.[c] | Catalyst | Cat. g | EO No.[d] | GC Area %[e] | Run Time min. |
|---|---|---|---|---|---|---|---|---|---|
| | | | | | | | 1 | 1.5 | |
| | | | | | | | 2 | 3.8 | |
| | | | | | | | 3 | 6.2 | |
| | | | | | | | 4 | 8.7 | |
| | | | | | | | 5 | 11.3 | |
| | | | | | | | 6 | 13.3 | |
| | | | | | | | 7 | 14.7 | |
| | | | | | | | 8 | 15.8 | |
| | | | | | | | 9 | 15.8 | |

[a]For each experiment, the total final reaction mixture weight was 150 g and the reaction temperature was 175° C. No alcohol or alcohol ethoxylate cocatalyst was used. Amount of catalyst used was 1.0% w/w to 2.0% w/w based on weight of final reaction mixture.
[b]Calculated from weight of final reaction mixture.
[c]These values obtained by nuclear magnetic resonance spectroscopy.
[d]Number of EO moieties per methyl laurate or methyl myristate molecule; 0 represents unreacted starting material.
[e]Normalized area %; calculated from g, chromatographic data.
[f]Aluminum-containing CCA catalyst; ratio of Ca:SO$_4$:Al is 5:1:1. The amount of catalyst used was 1.0% w/w based on weight of final reaction mixture.
[g]Titanium-containing CCA catalyst; ratio of Ca:SO$_4$:Ti is 5:1:2. The amount of catalyst used was 2.0% w/w based on weight of final reaction mixture.
[h]Titanium-containing CCA catalyst; ratio of Ca:SO$_4$:Ti is 4:1:2. The amount of catalyst used was 2.0% w/w based on weight of final reaction mixture.
[i]Aluminum-containing CCA catalyst, but prepared without 2-ethylhexanoic acid and ratio of Ca:SO$_4$:Al is 8:1:2. The amount of catalyst used was 2.0% w/w based on weight of final reaction mixture.

As can be seen from the data in Table 5, while the use of the process of Procedure 5 (Calcium Catalyst A with titanium alkoxide) does not result in as peaked a product as the use of aluminum alkoxide in the Calcium Catalyst A formulation, the process nonetheless results in shorter run times and requires less catalyst than prior art processes using catalysts such as sodium hydroxide, sodium methoxide or hydrotalcite. Moreover, the peaking of the product achieved using Calcium Catalyst A using titanium alkoxides is significantly greater than that achieved using such prior art processes employing NaOH or NaOMe as catalysts.

The data above clearly demonstrate that by using the process of the present invention, one can obtain ethoxylated methyl esters which exhibit a desired high degree of peaking, have higher conversion rates and, in the case of Calcium Catalyst A, greatly reduced reaction times. While the use of Calcium Catalyst B actually results, in some cases, in longer reaction times, nonetheless there is a significant increase in the amount of peaking obtained using Calcium Catalyst B as compared with other prior art processes and catalysts.

ALKOXYLATION OF FATTY-FATTY ESTERS

EXAMPLE 2

Various alkoxylated esters of Formula I type wherein $R_1$ is $C_2$ or greater were prepared using the process of the present invention as well as the prior art process employing NaOMe catalyst for comparative purposes to show that the process of the present invention is much more efficient in exhibiting higher conversion rates and efficiencies and in resulting in an alkoxylated ester which shows greater peaking than that obtained by the prior art process and catalyst.

Procedure 6—Typical Preparation of Ethoxylated (Fatty-Fatty) Ester Using NaOMe Catalyst A stainless steel autoclave is charged with the requisite amount of the starting material ester as determined by the desired weight percent ethylene oxide in the final product and the desired amount of NaOMe. For example, in a typical preparation, if the total final reaction mixture is 150 g, 0.75 g of NaOMe, i.e. 0.5 weight percent (2127 ppm total catalytic Na content) based on the total final weight of reaction mixture, is used. The mixture is heated under nitrogen to 110° C. at which time a vacuum is applied to produce a nitrogen sparge of 5 psi in the reactor. The reaction mixture is sufficiently dry after 20 minutes of sparging. The temperature is subsequently raised to 175° C. with nitrogen blanketing the reaction mixture. At 175° C., the reactor is optionally evacuated and ethylene oxide (EO) introduced to approximately 50 psi. Subsequent amounts of ethylene oxide are introduced into the reactor when the pressure drops as a result of ethoxylation. Temperature is maintained at or near 175° C. throughout the reaction. The catalyst is destroyed upon completion of the reaction by injection of the requisite amount of glacial acetic acid after cooling to approximately 80° C.

Procedure 7—Typical Preparation of Ethoxylated (Fatty-Fatty) Ester Using Calcium Catalyst A The procedure employed was the same as Procedure 6 with the exception that Calcium Catalyst A prepared substantially as per the teachings of U.S. Pat. No. 4,775,653 was employed and the catalyst was added to the starting material ester after drying. The amount of Catalyst A used was 2% by weight based on the final reaction mixture weight (720 ppm total catalytic combined Ca+Al content). Additionally, it was not necessary to destroy the catalyst by the addition of glacial acetic acid. To prepare Calcium Catalyst A(CCA), in general a mixture of 125 g ALFONIC® 1012-40$^2$ alcohol ethoxylate, 2 g 2-ethyl hexanoic acid, and 10.9 g, Ca(OH), was stirred in a stainless steel autoclave under a nitrogen atmosphere while concentrated $H_2SO_4$ (2 g) was added over a period of 10 minutes. Stirring was continued after $H_2SO_4$ addition for about 5 hours. The mixture was subsequently heated to 150° C. and sparged for 15 minutes with nitrogen to remove water. Upon cooling to about 125° C., 17.5 g of aluminum trialkoxide in which the alkoxide groups have an average chain length of 10 carbon atoms (mixed 2-30 carbon chain length) and containing about 6 percent-by-weight of aluminum was added, the mixture being maintained under nitrogen. The temperature was then raised to 190° C. at which time stripping of a portion of the alcohol from the aluminum alkoxide took place using a nitrogen sparge. Heating at 190° C. for an additional 0.5 hour followed by cooling under nitrogen to ambient temperature provided the active catalyst. The Calcium Catalyst A employed had a Ca:SO$_4$:Al ratio of 5:1:1 derived from calcium hydroxide, sulfuric acid and aluminum. The combined amount of Ca and Al in the catalyst was 0.054 g, i.e. the catalyst contained 3 percent-by-weight calcium and 0.6 percent-by-weight aluminum.

[2] Mixture of C$_{10}$-C$_{12}$ alcohols ethoxylated with 40 percent-by-weight ethylene oxide marketed by Vista Chemical Company.

Table 6 below shows comparative data obtained on several ethoxylated (fatty-fatty) esters made according to the process of the present invention using Procedure 7, i.e., employing Calcium Catalyst A, as compared with esters made using Procedure 6 (NaOMe catalyst). In all cases "final reaction mixture" means the combined weight of the starting material ester and the alkylene (ethylene) oxide.

TABLE 6

| Expt.[a] No. | Ester | EO % w/w[b] | Catalyst | Cat. g | Residual Starting Material (wt %) |
|---|---|---|---|---|---|
| 1 | Butyl Decanoate | 60 | CCA | 3.0[a] | 10.6[c] |
| 2 | Butyl Decanoate | 60 | NaOMe | 0.75 | 14.7[c] |
| 3 | Decyl Decanoate | 65 | NaOMe[d] | 0.75[a] | 9.5[c] |
| 4 | Decyl Docanoate | 65 | CCA[d] | 3.0 | 6.7[c] |

[a]For each experiment, the total final reaction mixture weight was 150 g and the reaction temperature was 175° C., unless specified otherwise.
[b]These values obtained by NMR.
[c]These values obtained by gas chromatography - mass spectromen.
[d]Four (4) percent-by-weight of Novel H 1216CO-60 also used. Novel II 1216CO-60 is a mixture of C$_{12}$-C$_{16}$ alcohols ethoxylated to 60 percent by weight ethylene oxide marketed by Vista Chemical Company.

As can be seen from the data in Table 6, the process of the present invention results in higher conversions as evidenced by lower residual starting material in the reaction mixture.

Figure 2:
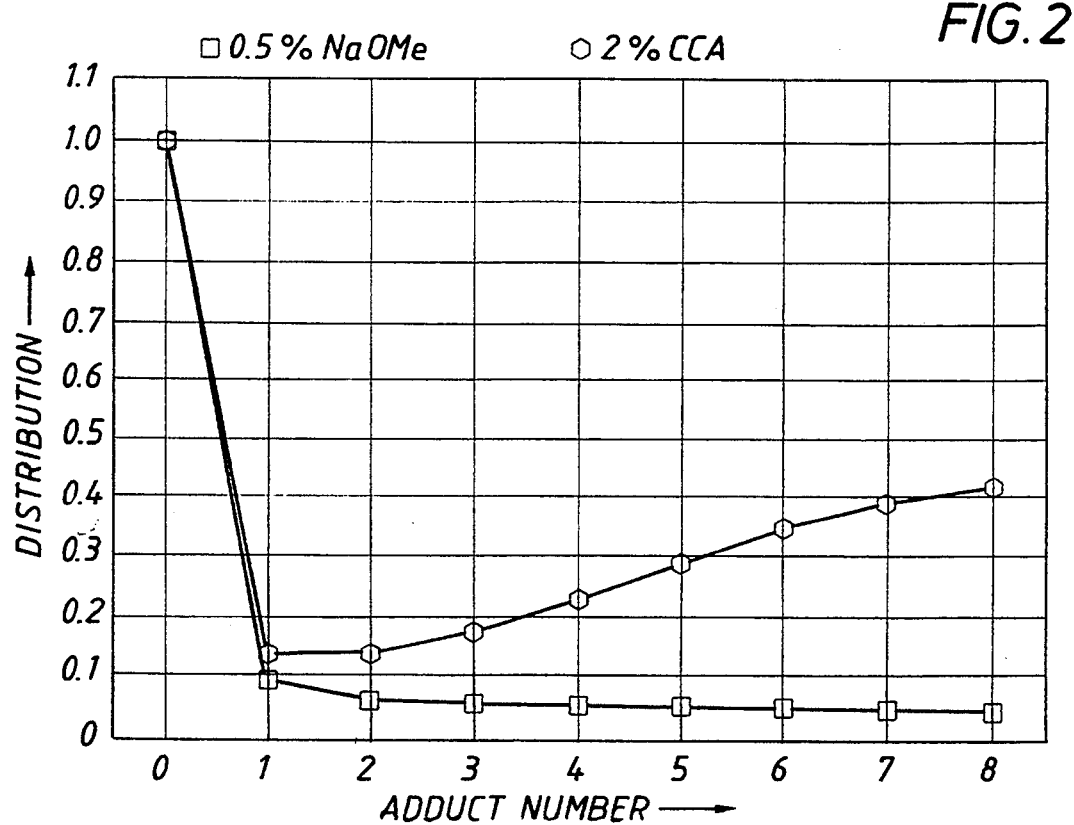
FIG. 2 is a graph comparing the distribution of the alkoxylated adducts of an ester made using the process of the present invention with an ester made using a prior art process.
Figure 3:
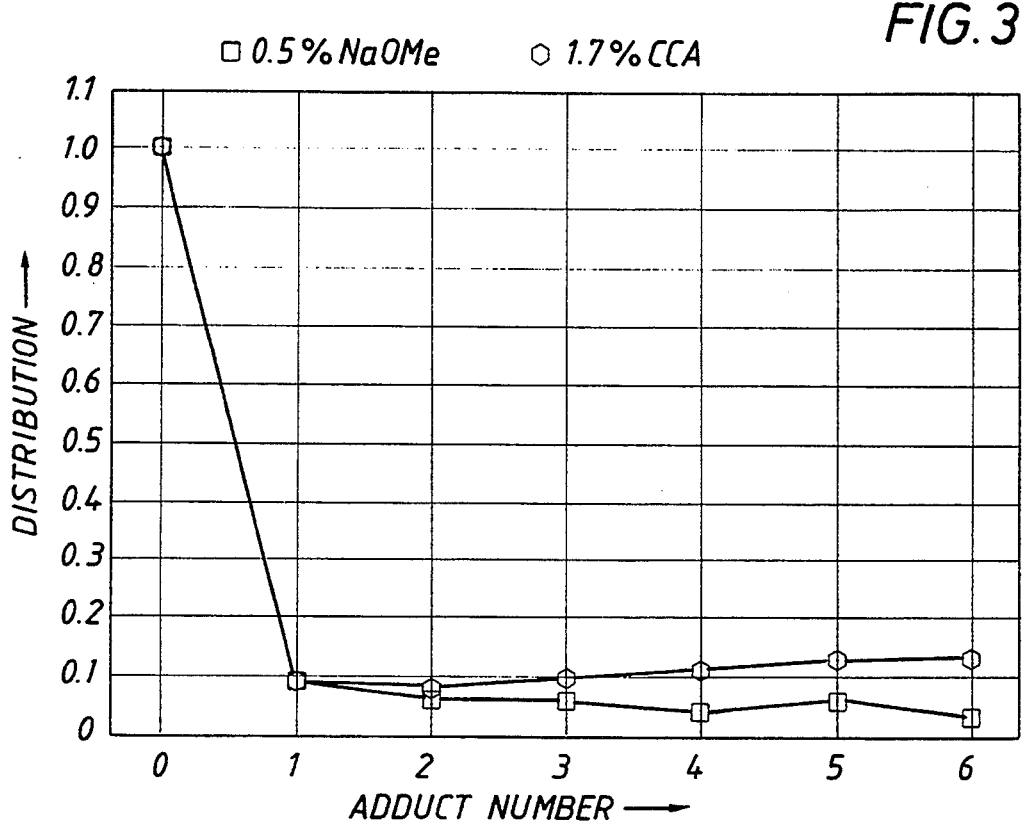
FIG. 3 is a graph similar to FIG. 2 as to another ester.

FIGS. 2 and 3 show a comparison, in terms of the degree of peaking, of alkoxylated fatty-fatty esters made in accordance with the present invention as compared with such esters made according to the prior art process using sodium methoxide. As can be seen in FIG. 2, using the process of the present invention, the esters made according to the process of the present invention exhibit significantly better peaking than the esters made according to the prior art process. Like results are shown in FIG. 3 using decyl decanoate as the starting material ester.

Procedure 7—Typical Preparation of. Ethoxylated (Fatty-Fatty) Ester Using Two-Step, One-Pot Process In this two-step, one-pot method, a stainless steel autoclave was charged with methyl myristate and Alfol ® 12$^L$ alcohol in a 1:1 mole ratio and heated under nitrogen to 85° C. The reactor was evacuated and Calcium Catalyst A, ~2 wt % based on final product weight, was then injected. Ethylene oxide was immediately added to a pressure of ~50 psig. Subsequent amounts of ethylene oxide were introduced into the reactor when the pressure dropped as a result of ethoxylation. The temperature was maintained at −85° C. throughout the addition. Afterwards, methanol was removed from the reaction mixture by heating to 200° C. and applying a vacuum sparge with nitrogen.

[1]A C$_{12}$ alcohol marketed by Vista Chemical Co.

Analysis confirmed that the ethoxylated myristate ester of the Alfol ® 12 alcohol was obtained. In a variation, the methyl myristate was left out of the alcohol ethoxylation step and introduced subsequent to the ethylene oxide addition. Again, analysis confirmed the presence of the ethoxylated myristate ester of the Alfol ® 12 alcohol.

As the above data demonstrate, by employing the process of the present invention, one can obtain alkoxylated (fatty-fatty) esters which exhibit a narrower distribution of the alkoxylated species. In addition, the present invention provides a process which exhibits higher conversion rates.

ALKOXYLATION OF ETHYLENE GLYCOL DIESTERS

Ethylene glycol diacetate and ethylene glycol di-n-butyrate, used as starting material esters, were commercially obtained. Ethylene glycol di-n-hexanoate, di-n-octanoate and di-n-decanoate were prepared, in the manner described below, by acylation of anhydrous ethylene glycol with the appropriate acyl chloride.

8—Preparation of Ethylene Glycol Diesters

Ethylene Glycol Di-n-hexanoate. Powdered imidazole (320.2 g, 3.78 mol) was placed in a 21, 3-necked round-bottomed flask equipped with an overhead mechanical stirrer, water cooled reflux condenser, 500 ml constant-pressure addition funnel, and a gas inlet under a constant sweep of N2. Anhydrous ethylene glycol (105 ml, 1.88 mol) was added and careful stirring was begun to mix the glycol and imidazole. This viscous slurry was heated in an oil bath to 95° C. (the imidazole completely dissolved by 85°–90° C.) and the N2 flow stopped. Then, hexanoyl chloride (511 ml, 3.66 mol) was added rapidly in a stream over a period of 40 minutes. The addition was mildly exothermic. A white precipitate formed immediately upon beginning acid chloride addition. The two-phase reaction mixture was stirred and heated at 120°–130° C. for 2 hours.

The reaction mixture was cooled to near room temperature in an ice-water bath, then 400 ml of saturated aqueous KHCO$_3$ was added carefully to minimize bumping. This was followed by 250 ml of deionized water. The two-phase mixture (upper clear yellow, lower cloudy white with some white precipitate) was stirred in the cold for about 5 min., then transferred to a 21 separatory funnel. Diethyl ether (200 ml) was added to the funnel and the reaction vessel was washed 2×100 ml with ether, the washings being added to the funnel. After separating the layers, the aqueous portion was extracted 4×150 ml with ether. The combined ethereal extracts were then sequentially washed 2×100 ml with deionized water and 2×150 ml with saturated aqueous KHCO$_3$, and dried overnight over anhydrous MgSO$_4$.

The MgSO$_4$, was removed by filtration and the ether removed by rotary evaporation to leave 470.3 g (98% crude yield) of clear, pale yellow oil. The crude product was distilled under vacuum to give 401.2 g (82.5% purified yield) of clear, colorless, mobile oil (bp 99 104° C./<1 mm Hg).

Ethylene Glycol Di-n-octanoate. Ethylene glycol di-n-octanoate was prepared as described for ethylene glycol di-n-hexanoate (except that heating was conducted at 140°– 150° C.) from octanoyl chloride (483 ml, 2.83 mol), anhydrous ethylene glycol (78 ml, 1.40 mol) and imidazole (193 g, 2.84 mol). Obtained 381.3 g (86.7% purified yield) of clear, colorless, mobile oil (bp 145°°148° C./<1 mm Hg).

Ethylene Glycol Di-n-decanoate. Ethylene glycol di-n-decanoate was prepared as described for ethylene glycol di-n-hexanoate (except that heating was conducted at 140°-150° C.) from decanoyl chloride (457 ml, 2.20 mol), anhydrous ethylene glycol (61 ml, 1.09 mol) and imidazole (153.5 g, 2.25 mol). Also, larger amounts of diethyl ether were required in the work-up to keep the crude diester dissolved since it is a solid. Obtained 352.4 g (87.0% crude yield) of light yellow solid, mp 37°-39° C. This material was used without further purification.

Procedure 8—Preparation of Ethylene Glycol Diester Ethoxylates

The ethoxylation procedure given below is typical of all of the diesters that were studied. In each case, the batch scale was 150 g. This weight was the final weight of the batch (after reaction) and included the weight of the diester and all the added ethylene oxide. It did not include the weight of added catalyst. However, the weight of catalyst used was calculated on the basis of the final batch weight of 150 g. For example, a catalyst loading of 2 wt % corresponds to addition of 3.0 g of catalyst to a batch that has a final weight of 150 g. Each reaction was conducted at 175° C. Co-catalyst was not employed.

Ethoxylation of Ethylene Glycol Di-n-butyrate Using Calcium Catalyst A. Ethylene glycol di-n-butytrate (60 g, 0.30 mol) was sealed in a tared stainless steel autoclave. The autoclave was purged 3×50 psig $N_2$ to remove atmospheric $O_2$ then pressured to 50 psig $N_2$. The diester was heated to 110° C., at which time it was sparged at this temperature under a flow of 60-65 ml/min (at 5 psig) $N_2$ for 15 minutes to remove residual moisture. The autoclave was pressured again to 50 psig $N_2$ and heated to 175° C. Next, the autoclave was evacuated to full vacuum and 3.0 g of Calcium Catalyst A (2 wt % based on the final batch weight of 150 g) was injected into the diester by syringe through a septum. Ethylene oxide (EO) was then added to a pressure of 40-45 psig EO and the ethoxylation reaction allowed to proceed. During the course of the reaction, EO was added automatically based on the pressure drop of EO in the autoclave vapor space (due to consumption of EO in the reaction). When the pre-determined amount of EO had been added, the reaction mixture was allowed to stir at 175° C. to ensure consumption of the remaining EO ("post-stir"). The reaction time was 62 minutes. Upon completion of the reaction, the autoclave was cooled to approx. 70° C. and the autoclave was purged 3×50 psig $N_2$ to remove residual EO. Finally, the autoclave and its contents were weighed together and the amount of added EO calculated.

Typically, Calcium Catalyst A has a catalytic metals content of 3.47 wt % Ca and 0.79 wt % Al (4.26 wt % total catalytic metals content in the catalyst). Thus, for this ethoxylation, the total catalytic metals content is 852 ppm Ca+Al.

Ethoxylation of Ethylene Glycol Di-n-butyrate Using Sodium Hydroxide Catalyst. Ethylene glycol di-n-butytrate (60 g, 0.30 mol) was ethoxylated essentially as described above using 6.0 g of 50 wt % aqueous NaOH (3.0 g of NaOH, 2 wt % based on the final batch weight of 150 g) as catalyst. Changes in the procedure that were specific to this catalyst included adding the NaOH to the diester prior to the initial sealing of the autoclave, and sparging at 110° C. under a flow of 60-65 ml/min (at 5 psig) N2 for 45 minutes to remove water added as part of the catalyst. The reaction time was 153 minutes.

The NaOH catalyst had a catalytic metal content of 57.5 wt % Na. Thus, for this ethoxylation, the total catalytic metal content was 11,495 ppm Na—13.5 times the total catalytic metals content of the ethoxylation done using Calcium Catalyst A.

Table 7 contains processing data for the ethylene glycol (EG) diester ethoxylates that were studied. Both Calcium Catalyst A (CCA) and standard (prior art) NaOH catalyst were used. The reaction times for ethoxylation using standard NaOH catalyst are much longer than when CCA is employed. This is particularly evident when one compares Experiments 2 and 3 to 10 and 11, respectively. The reaction time for EG dinecrate is much longer than for the other substrates. We believe this is due to the presence of a small amount of acetic acid contamination in the EG diacetate starting material. We have observed that free carboxylic acids (fatty acids) significantly retard the ethoxylation rate, until they are ethoxylated.

The amounts of NaOH catalyst used reflect the need to have large amounts of catalytic metal (Na) present in the reaction mixture to get reasonable reaction rates. For example, in comparing Experiments 3 and 11, each reaction used 2 wt % of catalyst —3.0 g of CCA and 3.0 g of NaOH (after accounting for the water in 50% aqueous NaOH). Since typically Calcium Catalyst A has a catalytic metals content of 3.47 wt % Ca and 0.79 wt % Al (4.26 wt % total catalytic metals content in the catalyst), the total catalytic metals content was 852 ppm Ca+Al in Experiment 3. In comparison, Experiment 11 had a total catalytic metal content of 11,495 ppm Na—13.5 times the total catalytic metals content of the ethoxylation done using Calcium Catalyst A.

Figure 4:
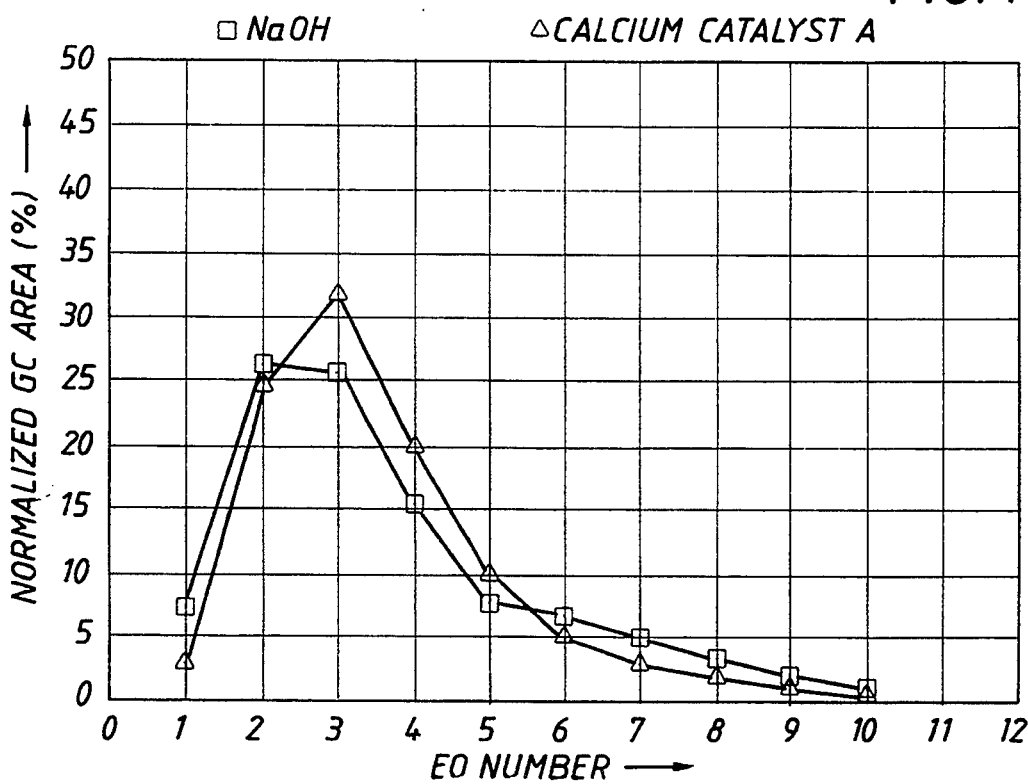
FIG. 4 is a graph showing a comparison of ethoxylated adducts of ethoxylated ethylene glycol diesters produced using the process of the present invention with such esters produced using a prior art process.

Table 8 presents EO distribution data for Experiments 2 and 10 (CCA and NaOH catalysts, respectively). These data are plotted in FIG. 4. The two distributions are quite similar. It is known in the literature that it is difficult to distinguish peaking distributions in short chain low-mole alcohol ethoxylates.

Figure 5:
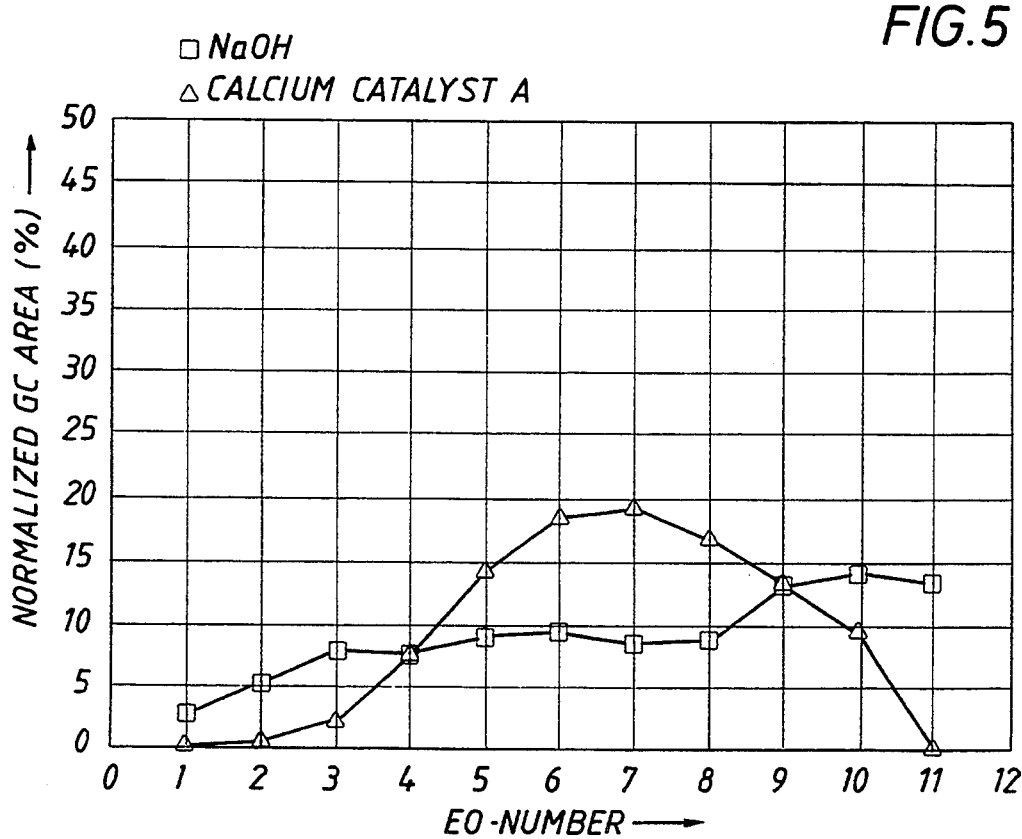
FIG. 5 is a graph similar to FIG. 4 but at a higher degree of ethoxylation.

Table 9 presents EO distribution data for high-mole diester ethoxylates. The data are plotted in FIG. 5. It is much easier to distinguish peaking for these ethoxylates. It is clear from FIG. 5 that CCA exhibits peaking while the standard NaOH catalyst does not. It is noted that the NaOH catalyzed ethoxylations exhibit lower conversions of starting material to product; and that NaOH catalyzed reactions have higher amounts of PEG (polyethylene glycol) (as evidenced by GC analysis).

Figure 6:
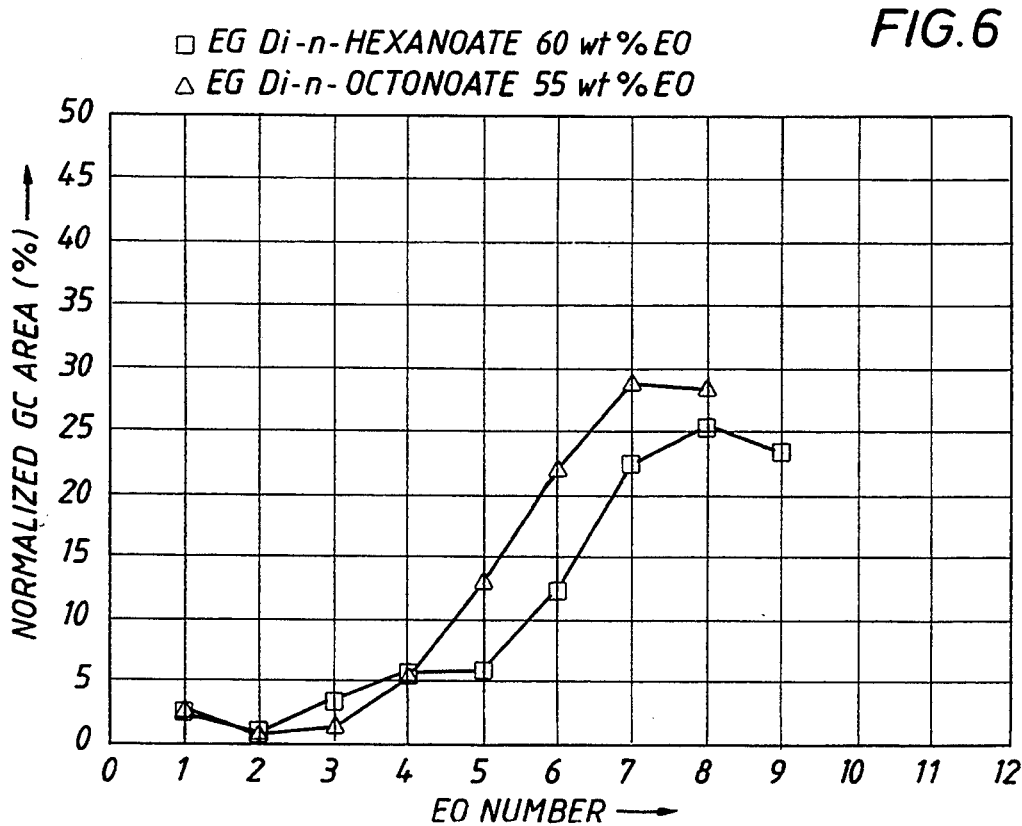
FIG. 6 is a graph showing the ethoxymer distribution in two different ethoxylated ethylene glycol diesters.

The above discussion has centered on ethylene glycol di-n-butyrate as starting material. This is because ethoxylates prepared from this diester are easy to analyze by GC. Diester ethoxylates with longer alkyl chains do not completely elute from the GC column. Two partial EO distributions for larger diester ethoxylates are presented graphically in FIG. 6. One can see that not all of the sample eluted from the column; the problem only gets worse for alkyl chains longer than Ca and EO amounts greater than 55 wt %.

In conclusion, ethoxylation of ethylene glycol diesters proceeds at a faster rate with Calcium Catalyst A than with the standard NaOH catalyst. CCA gives this faster rate with a much lower concentration of catalytic metals than NaOH. Also, CCA gives superior peaking, better starting material conversion to product, and lower amounts of by-products (e.g., PEG) as compared to the standard NaOH catalyst.

TABLE 7

PROCESSING DATA for ETHYLENE GLYCOL DIESTER ETHOXYLATES[a]

| Expt. No. | Diester | EO % w/w Target | EO % w/w Obsd.[b] | Catalyst[c] | Cat. g | Rxn Time min. |
|---|---|---|---|---|---|---|
| 1 | diacetate | 60 | 57.6 | CCA | 3.0 | 187[d] |
| 2 | dibutyrate | 35 | 33.6 | " | 6.0 | 52 |
| 3 | dibutyrate | 60 | 57.6 | " | 3.0 | 62 |
| 4 | dihexanoate | 60 | 57.9 | " | 3.0 | 75 |
| 5 | dihexanoate | 65 | 63.5 | " | 3.0 | 57 |
| 6 | dioctanoate | 55 | 53.8 | " | 3.0 | 42 |
| 7 | dioctanoate | 60 | 58.7 | " | 3.0 | 39 |
| 8 | didecanoate | 60 | 57.7 | " | 4.5 | 94 |
| 9 | distearate | 65 | 63.7 | " | 3.0 | 51 |
| 10 | dibutyrate | 35 | 31.6 | 50% NaOH | 6.1 | 222 |
| 11 | dibutyrate | 60 | 56.6 | 50% NaOH | 6.0 | 153 |

[a]For each experiment, the total final product weight was 150 g and the reaction temperature was 175° C.
[b]Calculated from weight of final product.
[c]CCA = Calcium Catalyst A
[d]Starting material contaminated with a small amount of acetic acid.

TABLE 8

COMPARATIVE EXAMPLES: LOW-MOLE ETHYLENE GLYCOL DIESTER ETHOXYLATES[a]

| Expt. No. | Diester | EO % w/w Target | EO % w/w Obsd.[b] | Catalyst[c] | Cat. g | EO No.[d] | GC Area %[e] | Rxn Time min. |
|---|---|---|---|---|---|---|---|---|
| 2 | dibutyrate | 35 | 33.6 | CCA | 6.0 | 1 | 2.2 | 52 |
|   |   |   |   |   |   | 2 | 24.4 |   |
|   |   |   |   |   |   | 3 | 31.8 |   |
|   |   |   |   |   |   | 4 | 20.1 |   |
|   |   |   |   |   |   | 5 | 10.3 |   |
|   |   |   |   |   |   | 6 | 5.4 |   |
|   |   |   |   |   |   | 7 | 2.9 |   |
|   |   |   |   |   |   | 8 | 1.6 |   |
|   |   |   |   |   |   | 9 | 0.9 |   |
|   |   |   |   |   |   | 10 | 0.5 |   |
| 10 | dibutyrate | 35 | 31.6 | 50% NaOH | 6.1 | 1 | 7.2 | 222 |
|   |   |   |   |   |   | 2 | 26.0 |   |
|   |   |   |   |   |   | 3 | 25.8 |   |
|   |   |   |   |   |   | 4 | 15.4 |   |
|   |   |   |   |   |   | 5 | 7.8 |   |
|   |   |   |   |   |   | 6 | 7.0 |   |
|   |   |   |   |   |   | 7 | 5.1 |   |
|   |   |   |   |   |   | 8 | 3.1 |   |
|   |   |   |   |   |   | 9 | 1.7 |   |
|   |   |   |   |   |   | 10 | 0.9 |   |

[a]For each experiment, the total final product weight was 150 g and the reaction temperature was 175° C. Amount of catalyst used was based on weight of final product.
[b]Calculated from weight of final product.
[c]CCA = Calcium Catalyst A.
[d]Number of EO moieties per diester; 1 represents unreacted starting material.
[e]Normalized area %; calculated from gas chromatographic data.

TABLE 9

COMPARATIVE EXAMPLES: HIGH-MOLE ETHYLENE GLYCOL DIESTER ETHOXYLATES[a]

| Expt. No. | Diester | EO % w/w Target | EO % w/w Obsd.[b] | Catalyst[c] | Cat. g | EO No.[d] | GC Area %[e] | Rxn Time min. |
|---|---|---|---|---|---|---|---|---|
| 3 | dibutyrate | 60 | 57.6 | CCA | 3.0 | 1 | tr[f] | 62 |
|   |   |   |   |   |   | 2 | 0.3 |   |
|   |   |   |   |   |   | 3 | 2.0 |   |
|   |   |   |   |   |   | 4 | 7.7 |   |
|   |   |   |   |   |   | 5 | 14.0 |   |
|   |   |   |   |   |   | 6 | 17.9 |   |
|   |   |   |   |   |   | 7 | 18.7 |   |
|   |   |   |   |   |   | 8 | 16.6 |   |
|   |   |   |   |   |   | 9 | 13.3 |   |
|   |   |   |   |   |   | 10 | 9.7 |   |
|   |   |   |   |   |   | 11 | tr[f] |   |
| 11 | dibutyrate | 60 | 56.6 | 50% NaOH | 6.0 | 1 | 2.5 | 153 |
|   |   |   |   |   |   | 2 | 5.3 |   |
|   |   |   |   |   |   | 3 | 7.6 |   |
|   |   |   |   |   |   | 4 | 7.3 |   |
|   |   |   |   |   |   | 5 | 9.4 |   |
|   |   |   |   |   |   | 6 | 9.8 |   |
|   |   |   |   |   |   | 7 | 8.6 |   |
|   |   |   |   |   |   | 8 | 9.0 |   |
|   |   |   |   |   |   | 9 | 13.1 |   |
|   |   |   |   |   |   | 10 | 14.1 |   |

TABLE 9-continued
COMPARATIVE EXAMPLES: HIGH-MOLE ETHYLENE GLYCOL DIESTER ETHOXYLATES[a]

| Expt. No. | EO % w/w Diester | Target | Obsd.[b] | Catalyst[c] | Cat. g | EO No.[d] | GC Area %[e] | Rxn Time min. |
|---|---|---|---|---|---|---|---|---|
| | | | | | | 11 | 13.4 | |

[a] For each experiment, the total final product weight was 150 g and the reaction temperature was 175° C. Amount of catalyst used was based on weight of final product.
[b] Calculated from weight of final product.
[c] CCA = Calcium Catalyst A.
[d] Number of EO moieties per diester; 1 represents unreacted starting material.
[e] Normalized area; calculated from gas chromatographic data.
[f] tr = trace

ALKOXYLATION OF TRIESTERS (TRIGLYCERIDES)

Procedure 8 above was generally employed to produce ethoxylated triesters using Calcium Catalyst A and NaOH, respectively.

Ethoxylation of Trilaurin

Trilaurin was ethoxylated, in two separates runs, to a level of 70 percent-by-weight ethylene oxide and 67.8 percent-by-weight ethylene oxide. $^1$HNMR analysis confirmed that there was complete conversion of starting material using both Calcium Catalyst A and NaOH. The analysis also showed the incorporation of the oxyethylene groups into the trilaurin starting material to produce the ethoxylated trilaurin.

Ethoxylation of Tributyrin

Tributyrin as a starting material triester was ethoxylated using Calcium Catalyst A and potassium t-butoxide. In both cases, a co-catalyst comprising glycerol monooleate was also employed. Using both catalysts, the tributyrin was ethoxylated to the 60 percent-by-weight ethylene oxide level and the 57.8 percent-by-weight ethylene oxide. $^1$HNMR analysis indicated complete conversion of starting material in all cases. The analysis also showed the presence of oxyethylene groups in the backbone of the tributyrin structure.

As can be seen from the above data, the process of the present invention provides a vastly improved method for alkoxylating monoesters, diesters, triesters and other polyesters. The process, in general, leads to alkoxylated products that are more peaked than can be obtained with prior art processes. In addition, and as a general rule, the process of the present invention exhibits higher conversion rates, reduced reaction times and lower make of by-products than can be obtained with prior art processes for alkoxylating esters.

The alkoxylated esters produced by the process of the present invention find widespread use in surfactants, detergents and similar applications, as well as fatty acid ethoxylate replacements. Thus, by the desired degree of tailoring, the alkoxylated esters can be used in such diverse applications as laundry detergents, hand soaps, shampoos, hard surface cleaners, bath soaps, etc. For example, the alkoxylated monoesters wherein R' is —CH$_3$ provide a surfactant exhibiting excellent mildness characteristics. In particular, ethoxylated methyl myristate and stripped methyl coconate, both ethoxylated to the 60 percent-by-weight ethylene oxide, exhibit mildness characteristics as good as a commercially available fatty acid ethoxylate, i.e., lauric acid ethoxylated with 66 percent-by-weight ethylene oxide. The alkoxylated esters produced herein are easily biodegradable and exhibit lower levels of aquatic toxicity than commonly used surfactants such as alkoxylated alcohols.

As noted above, the alkoxylated esters of the present invention also exhibit good hard surface cleaning characteristics. In particular, tests have shown that the alkoxylated monoesters wherein R' is CH$_3$ and made according to the process of the present invention are generally as good as, or better than, commercially available hard surface cleaning agents when tested at the 3 percent-by-weight level in water. (In all cases, for comparative purposes, comparisons were made against ALFONIC® 610-50AE, an industry standard in hard surface cleaners.) Further, alkoxylated esters made according to the process of the present invention exhibit better hard surface cleaning ability than alkoxylated esters made using prior art catalysts such as sodium methoxide. The methyl esters of hexanoic and octanoic acid ethoxylated to the 55 and 60 percent-by-weight levels using the process of the present invention demonstrate better hard surface cleaning ability than comparable samples made using sodium methoxide as a catalyst or several commercially available compounds considered to be good hard surface cleaning agents.

Hard surface cleaning ability was also exhibited by the alkoxylated monoesters wherein R' is C$_2$ or greater and the triesters. Several of the alkoxylated ethylene glycol diesters prepared according to the process of the present invention (tested at a 3% concentration in water) performed very well on graphite soil.

It will be apparent that by mixing various of the alkoxylated esters prepared according to the process of the present invention, one can tailor the end product to achieve desired results. For example, by blending an alkoxylated ester that exhibits good mildness characteristics with an alkoxylated ester that exhibits good hard surface cleaning ability, one can obtain a surfactant composition that, although mild to the skin, exhibits good hard surface cleaning ability.

The foregoing disclosure and description of the invention is illustrative and explanatory thereof and various changes may be made within the scope of the appended claims without departing from the spirit of the invention.

What is claimed is:

1. A process for producing alkoxylated esters selected from the group consisting of alkoxylated monoesters having the formula:

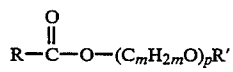
(I)

alkoxylated ethylene glycol diesters having the formula:

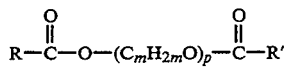 (II)

and alkoxylated triesters having the formula:

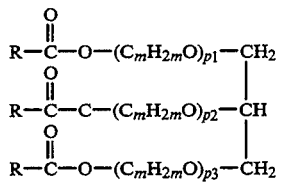 (III)

wherein m is from 2 to 4, p, $p_1$, $p_2$ and $P_3$ are each from about 1 to about 50, and R and R' are each an organic radical containing from about 1 to about 30 carbon atoms, comprising reacting an alkylene oxide containing from 2 to 4 carbon atoms with an ester starting material containing a compound selected from the group consisting of mono-esters having the formula:

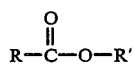 (IV)

ethylene glycol diesters having the formula:

 (V)

and triesters having the formula:

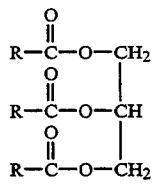 (VI)

respectively, said reaction being conducted at a temperature of from about 80° C. to about 200° C. and in the presence of a catalytically effective amount of a catalyst selected from the group consisting of (1) Calcium Catalyst A formed by reacting a reactant mixture comprising an alkoxylated alcohol mixture containing compounds having the general formula:

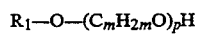 (VII)

wherein $R_1$ is an organic radical containing from about 1 to about 30 carbon atoms, a calcium-containing compound which is at least partially dispersible in said alkoxylated alcohol mixture, an inorganic acid compound, and a metal alkoxide of a Lewis acidic metal, said calcium-containing compound and said alkoxylated alcohol mixture being mixed prior to addition of said metal alkoxide, said reactant mixture being heated to a temperature and for a time sufficient to effect at least a partial exchange reaction between the alkoxide groups of said metal alkoxide and said hydroxyl groups of said alkoxylated alcohol, (2) Calcium Catalyst B formed by solubilizing, at least partially, a calcium-containing compound with an activator having the formula:

$$Z_a-X-Q-Y-Z'_b \quad \text{(IX)}$$

wherein X and Y are the same or different electronegative, hetero-atoms selected from the group consisting of oxygen, nitrogen, sulfur and phosphorus, a and b are the same or different integers satisfying the valency requirements of X and Y, Q is an organic radical which is electropositive or essentially neutral relative as to X and/or Y, and Z and Z' are the same or different and are either hydrogen or an organic radical which does not prevent said solubilizing and (3) mixtures of Calcium Catalyst A and Calcium Catalyst B.

2. The process of claim 1 wherein said calcium-containing compound is selected from the group consisting of calcium oxide, calcium hydroxide and mixtures thereof.

3. The process of claim 1 wherein R is a hydrocarbon radical containing from about 1 to about 30 carbon atoms.

4. The process of claim 1 wherein m is 2.

5. The process of claim 1 wherein p is from about 1 to about 15.

6. The process of claim 1 wherein a blend of compounds having the formula:

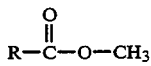

is employed as the ester starting material.

7. The process of claim 6 wherein said blend of compounds is derived from a natural source.

8. The process of claim 1 wherein said reaction is conducted at a pressure from about subambient to about 100 psi.

9. The process of claim 1 wherein the catalyst is Calcium Catalyst A, said catalyst being present in an amount of from about 0.01 to about 20 percent-by-weight of the combined weight of ester starting material and alkylene oxide.

10. The process of claim 1 wherein said catalyst is Calcium Catalyst B, said catalyst being present in an amount of from about 3 to about 90 percent-by-weight of the combined weight of ester starting material and alkylene oxide.

11. The process of claim 1 wherein said inorganic acid compound comprises an inorganic acid.

12. The process of claim 11 wherein said inorganic acid comprises sulfuric acid.

13. The process of claim 1 wherein said inorganic acid compound comprises an acid salt.

14. A process for producing alkoxylated esters selected from the group consisting of alkoxylated mono-esters having the formula:

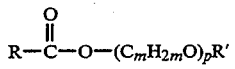

and alkoxylated ethylene glycol diesters having the formula:

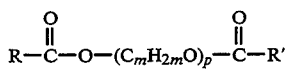

wherein m is from 2 to 4, p is from about 1 to about 50, and R and R' are each an organic radical containing from about 1 to about 30 carbon atoms, comprising reacting an alkylene oxide containing from 2 to 4 carbon atoms with an ester starting material containing a compound selected from the group consisting of monoesters having the formula:

$$R-\overset{O}{\underset{\|}{C}}-O-R'$$

and ethylene glycol diesters having the formula:

$$R-\overset{O}{\underset{\|}{C}}-O-CH_2CH_2O-\overset{O}{\underset{\|}{C}}-R'$$

respectively, said reaction being conducted at a temperature of from about 80° C. to about 200° C. and in the presence of a catalytically effective amount of a catalyst selected from the group consisting of (1) Calcium Catalyst A formed by reacting a reactant mixture comprising an alkoxylated alcohol mixture containing compounds having the general formula:

$$R_1-O-(C_mH_{2m}O)_pH$$

wherein $R_1$ is an organic radical containing from about 1 to about 30 carbon atoms, a calcium-containing compound which is at least partially dispersible in said alkoxylated alcohol mixture, an inorganic acid compound, and a metal alkoxide of a Lewis acidic metal, said calcium-containing compound and said alkoxylated alcohol mixture being mixed prior to addition of said metal alkoxide, said reactant mixture being heated to a temperature and for a time sufficient to effect at least a partial exchange reaction between the alkoxide groups of said metal alkoxide and said hydroxyl groups of said alkoxylated alcohol, (2) Calcium Catalyst B formed by solubilizing, at least partially, a calcium-containing compound with an activator having the formula:

$$Z_a-X-Q-Y-Z'_b$$

wherein X and Y are the same or different electronegative, hetero-atoms selected from the group consisting of oxygen, nitrogen, sulfur and phosphorus, a and b are the same or different integers satisfying the valency requirements of X and Y, Q is an organic radical which is electropositive or essentially neutral relative as to X and/or Y, and Z and Z' are the same or different and are either hydrogen or an organic radical which does not prevent said solubilizing and (3) mixtures of Calcium Catalyst A and Calcium Catalyst B, said alkoxylated esters produced being characterized by having a molecular weight distribution such that the portion of the mixture having 3 or more oxyalkylene groups per ester linkage than the most prevalent alkoxylation species is less than 50 percent-by-weight of the mixture and the portion of the mixture having fewer oxyalkylene groups per ester linkage by 3 or more oxyalkylene groups than the most prevalent alkoxylation species is less than about 25 percent-by-weight.

15. The process of claim, 14 wherein the portion of the mixture having fewer oxyalkylene groups per ester linkage by 3 or more oxyalkylene groups than the most prevalent alkoxylation species is less than about 15 percent-by-weight.

16. A process for producing alkoxylated esters having the formula:

$$R-\overset{O}{\underset{\|}{C}}-O-(C_mH_{2m}O)_pR'$$

wherein m is from 2 to 4, p is from about 1 to about 50, and R is an organic radical containing from about 1 to about 30 carbon atoms and R' is an organic radical containing from about 1 to about 5 carbon atoms, comprising reacting an alkylene oxide containing from 2 to 4 carbon atoms with an alcohol having the formula:

$$R'-OH$$

to produce an alkoxylated alcohol having the formula:

$$R'-O-(C_mH_{2m}O)_p-H$$

and, reacting said alkoxylated alcohol with a starting material ester having the formula:

$$R-\overset{O}{\underset{\|}{C}}-O-R''$$

wherein R' is an organic radical containing from 1 to 5 carbon atoms to produce the ester of Formula I, said reaction between said alcohol and alkylene oxide and said alkoxylated alcohol and said starting material ester being conducted in the same reactor vessel, said reactions being conducted at a temperature of from about 60° C. to about 200° C. and in the presence of a catalytically effective amount of a catalyst selected from the group consisting of (1) Calcium Catalyst A formed by reacting a reactant mixture comprising an alkoxylated alcohol mixture containing compounds having the general formula:

$$R_1-O-(C_mH_{2m}O)_pH$$

wherein $R_1$ is an organic radical containing from about 1 to about 30 carbon atoms, a calcium-containing compound which is at least partially dispersible in said alkoxylated alcohol mixture, an inorganic acid compound, and a metal alkoxide of a Lewis acidic metal, said calcium-containing compound and said alkoxylated alcohol mixture being mixed prior to addition of said metal alkoxide, said reactant mixture being heated to a temperature and for a time sufficient to effect at least a partial exchange reaction between the alkoxide groups of said metal alkoxide and said hydroxyl groups of said alkoxylated alcohol, (2) Calcium Catalyst B formed by solubilizing, at least partially, a calcium-containing compound with an activator having the formula:

$$Z_a-X-Q-Y-Z'_b$$

wherein X and Y are the same or different electronegative, hetero-atoms selected from the group consisting of oxygen, nitrogen, sulfur and phosphorus, a and b are the same or different integers satisfying the valency requirements of X and Y, Q is an organic radical which is electropositive or essentially neutral relative as to X and/or Y, and Z and Z' are the same or different and are either hydrogen or an organic radical which does not prevent said solubilizing and (3) mixtures of Calcium Catalyst A and Calcium Catalyst B.

17. The process of claim 16 wherein said calcium-containing compound is selected from the group consisting of calcium oxide, calcium hydroxide and mixtures thereof.

18. The process of claim 16 wherein R is a hydrocarbon radical containing from about 1 to about 30 carbon atoms and R" is a methyl group.

19. The process of claim 16 wherein m is 2.

20. The process of claim 16 wherein p is from about 1 to about 50.

21. The process of claim 16 wherein the catalyst is Calcium Catalyst A.

22. The process of claim 16 wherein said catalyst is Calcium Catalyst B.

23. The process of claim 16 wherein said inorganic acid compound comprises an inorganic acid.

24. The process of claim 23 wherein said inorganic acid comprises sulfuric acid.

25. The process of claim 16 wherein said inorganic acid compound comprises an acid salt.

* * * * *

UNITED STATES PATENT AND TRADEMARK OFFICE
CERTIFICATE OF CORRECTION

PATENT NO. : 5,386,045
DATED : January 31, 1995
INVENTOR(S) : Upali Weerasooriya, et al.

It is certified that error appears in the above-indentified patent and that said Letters Patent is hereby corrected as shown below:

In column 31, line 16, delete "P3" and insert therefor --$P_3$--.

In column 33, line 64, delete the comma after "claim".

Signed and Sealed this

Twenty-fifth Day of April, 1995

*Attest:*

BRUCE LEHMAN

*Attesting Officer*   *Commissioner of Patents and Trademarks*